(12) United States Patent
Akilian et al.

(10) Patent No.: US 12,076,041 B2
(45) Date of Patent: Sep. 3, 2024

(54) RECIPROCATING ROTARY SURGICAL CUTTING DEVICE AND SYSTEM FOR TISSUE RESECTING, AND METHOD FOR ITS USE

(71) Applicant: Covidien LP, Mansfield, MA (US)

(72) Inventors: Mireille Akilian, Candia, NH (US); Tejas Inamdar, San Francisco, CA (US)

(73) Assignee: Covidien LP, Mansfield, MA (US)

( * ) Notice: Subject to any disclaimer, the term of this patent is extended or adjusted under 35 U.S.C. 154(b) by 177 days.

(21) Appl. No.: 17/527,074

(22) Filed: Nov. 15, 2021

(65) Prior Publication Data

US 2022/0071652 A1 Mar. 10, 2022

Related U.S. Application Data

(63) Continuation of application No. 16/407,291, filed on May 9, 2019, now Pat. No. 11,172,954, which is a continuation of application No. 15/221,967, filed on Jul. 28, 2016, now Pat. No. 10,299,819.

(51) Int. Cl.
*A61B 17/32* (2006.01)
*A61B 17/00* (2006.01)
*A61B 17/3207* (2006.01)

(52) U.S. Cl.
CPC .......... *A61B 17/32002* (2013.01); *A61B 17/320783* (2013.01); *A61B 2017/00982* (2013.01); *A61B 2017/320024* (2013.01); *A61B 2017/320028* (2013.01); *A61B 2217/007* (2013.01)

(58) Field of Classification Search
CPC ............... A61B 17/29; A61B 17/3207; A61B 17/320016; A61B 17/3205; A61B 17/320783; A61B 2017/32004; A61B 2017/320024; A61B 2017/320028
See application file for complete search history.

(56) References Cited

U.S. PATENT DOCUMENTS

| 1,585,934 A | 5/1926 | Muir |
| 1,666,332 A | 4/1928 | Hirsch |
| 1,831,786 A | 11/1931 | Duncan |
| 2,708,437 A | 5/1955 | Hutchins |

(Continued)

FOREIGN PATENT DOCUMENTS

| EP | 1753350 B1 | 8/2014 |
| WO | 2015023965 A1 | 2/2015 |

OTHER PUBLICATIONS

Extended European Search Report issued in corresponding application No. 17183474.0 dated Nov. 6, 2017.

*Primary Examiner* — Tuan V Nguyen
(74) *Attorney, Agent, or Firm* — Carter, DeLuca & Farrell LLP

(57) ABSTRACT

An endoscopic tissue resecting system that includes a reciprocating rotary surgical instrument for cutting tissue that includes a planetary gear assembly to vary rotational speed. A method of cutting and detaching tissue includes positioning an outer member such that tissue is located within a window in the outer member, engaging the tissue with an inner member, and simultaneously rotating at an increased speed relative to a rotary driver and translating the inner member to cut the tissue. A tangential cutting force is applied to the tissue with the inner member to mechanically cut and detach the tissue.

19 Claims, 19 Drawing Sheets

(56) References Cited

U.S. PATENT DOCUMENTS

| | | |
|---|---|---|
| 3,297,022 A | 1/1967 | Wallace |
| 3,686,706 A | 8/1972 | Finley |
| 3,734,099 A | 5/1973 | Bender et al. |
| 3,791,379 A | 2/1974 | Storz |
| 3,812,855 A | 5/1974 | Banko |
| 3,835,842 A | 9/1974 | Iglesias |
| 3,850,162 A | 11/1974 | Iglesias |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman et al. |
| 4,146,405 A | 3/1979 | Timmer et al. |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent et al. |
| 4,261,346 A | 4/1981 | Wettermann |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,284 A | 7/1986 | Arakawa et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Thimsen et al. |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk-Burleson et al. |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,027,792 A | 7/1991 | Meyer |
| 5,037,386 A | 8/1991 | Marcus et al. |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A | 12/1992 | Sakashita et al. |
| 5,176,677 A | 1/1993 | Wuchinich |
| 5,195,541 A | 3/1993 | Obenchain |
| 5,226,910 A | 7/1993 | Kajiyama et al. |
| 5,244,459 A | 9/1993 | Hill |
| 5,254,117 A | 10/1993 | Rigby et al. |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brody |
| 5,304,118 A | 4/1994 | Trese et al. |
| 5,312,399 A | 5/1994 | Hakky et al. |
| 5,312,425 A | 5/1994 | Evans et al. |
| 5,312,430 A | 5/1994 | Rosenbluth et al. |
| 5,320,091 A | 6/1994 | Grossi et al. |
| 5,347,992 A | 9/1994 | Pearlman et al. |
| 5,350,390 A | 9/1994 | Sher |
| 5,364,395 A | 11/1994 | West, Jr. |
| 5,374,253 A | 12/1994 | Burns, Sr. et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,409,453 A | 4/1995 | Lundquist et al. |
| 5,411,513 A | 5/1995 | Ireland et al. |
| 5,421,819 A | 6/1995 | Edwards et al. |
| 5,425,376 A | 6/1995 | Banys et al. |
| 5,429,601 A | 7/1995 | Conley et al. |
| 5,435,805 A | 7/1995 | Edwards et al. |
| 5,443,476 A | 8/1995 | Shapiro |
| 5,449,356 A | 9/1995 | Walbrink et al. |
| 5,456,673 A | 10/1995 | Ziegler et al. |
| 5,456,689 A | 10/1995 | Kresch et al. |
| 5,483,951 A | 1/1996 | Frassica et al. |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,563,481 A | 10/1996 | Krause |
| 5,569,164 A | 10/1996 | Lurz |
| 5,569,254 A | 10/1996 | Carlson et al. |
| 5,569,284 A | 10/1996 | Young et al. |
| 5,575,756 A | 11/1996 | Karasawa et al. |
| 5,591,187 A | 1/1997 | Dekel |
| 5,601,583 A | 2/1997 | Donahue et al. |
| 5,601,603 A | 2/1997 | Illi |
| 5,602,449 A | 2/1997 | Krause et al. |
| 5,603,332 A | 2/1997 | O'Connor |
| 5,630,798 A | 5/1997 | Beiser et al. |
| 5,649,547 A | 7/1997 | Ritchart et al. |
| 5,669,927 A | 9/1997 | Boebel et al. |
| 5,672,945 A | 9/1997 | Krause |
| 5,674,179 A | 10/1997 | Bonnet et al. |
| 5,676,497 A | 10/1997 | Kim |
| 5,695,448 A | 12/1997 | Kimura et al. |
| 5,702,420 A | 12/1997 | Sterling et al. |
| 5,709,698 A | 1/1998 | Adams et al. |
| 5,730,752 A | 3/1998 | Alden et al. |
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |
| 5,775,333 A | 7/1998 | Burbank et al. |
| 5,782,849 A | 7/1998 | Miller |
| 5,792,167 A * | 8/1998 | Kablik ............... A61M 3/0201 606/180 |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |

(56) References Cited

U.S. PATENT DOCUMENTS

| | | |
|---|---|---|
| 5,916,229 A | 6/1999 | Evans |
| 5,925,055 A | 7/1999 | Adrian et al. |
| 5,928,163 A | 7/1999 | Roberts et al. |
| 5,944,668 A | 8/1999 | Vancaillie et al. |
| 5,947,990 A | 9/1999 | Smith |
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A | 2/2000 | Lovato et al. |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,094 A | 7/2000 | Clifford, Jr. et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,171,316 B1 | 1/2001 | Kovac et al. |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,312,441 B1 * | 11/2001 | Deng ............... A61B 17/32002 606/170 |
| 6,315,714 B1 | 11/2001 | Akiba |
| 6,358,200 B1 | 3/2002 | Grossi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,471,639 B2 | 10/2002 | Rudischhauser et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,663,641 B1 | 12/2003 | Kovac et al. |
| 6,712,773 B1 | 3/2004 | Viola |
| 6,824,544 B2 | 11/2004 | Boebel et al. |
| 6,837,847 B2 | 1/2005 | Ewers et al. |
| 7,025,720 B2 | 4/2006 | Boebel et al. |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1 | 7/2007 | Emanuel |
| 7,510,563 B2 | 3/2009 | Cesarini et al. |
| 7,763,033 B2 | 7/2010 | Gruber et al. |
| 7,922,737 B1 | 4/2011 | Cesarini et al. |
| 8,062,214 B2 | 11/2011 | Shener et al. |
| 8,419,626 B2 | 4/2013 | Shener-Irmakoglu et al. |
| 8,574,253 B2 | 11/2013 | Gruber et al. |
| 8,663,264 B2 | 3/2014 | Cesarini et al. |
| 8,678,999 B2 | 3/2014 | Isaacson |
| 8,840,626 B2 | 9/2014 | Adams et al. |
| 8,852,085 B2 | 10/2014 | Shener-Irmakoglu et al. |
| 8,893,722 B2 | 11/2014 | Emanuel |
| 8,932,208 B2 | 1/2015 | Kendale et al. |
| 8,951,274 B2 | 2/2015 | Adams et al. |
| 9,060,800 B1 | 6/2015 | Cesarini et al. |
| 9,060,801 B1 | 6/2015 | Cesarini et al. |
| 9,066,745 B2 | 6/2015 | Cesarini et al. |
| 9,072,431 B2 | 7/2015 | Adams et al. |
| 9,089,358 B2 | 7/2015 | Emanuel |
| 9,125,550 B2 | 9/2015 | Shener-Irmakoglu et al. |
| 9,155,454 B2 | 10/2015 | Sahney et al. |
| 10,299,819 B2 | 5/2019 | Akilian et al. |
| 11,172,954 B2 | 11/2021 | Akilian et al. |
| 2001/0031975 A1 * | 10/2001 | Whitman ............... A61B 34/71 606/167 |
| 2001/0039963 A1 | 11/2001 | Spear et al. |
| 2001/0047183 A1 | 11/2001 | Privitera et al. |
| 2002/0058859 A1 | 5/2002 | Brommersma |
| 2002/0165427 A1 | 11/2002 | Yachia et al. |
| 2003/0050603 A1 | 3/2003 | Todd |
| 2003/0050638 A1 | 3/2003 | Yachia et al. |
| 2003/0078609 A1 | 4/2003 | Finlay et al. |
| 2003/0114875 A1 | 6/2003 | Sjostrom |
| 2003/0225344 A1 | 12/2003 | Miller |
| 2004/0010258 A1 | 1/2004 | Carusillo et al. |
| 2004/0092980 A1 * | 5/2004 | Cesarini ........... A61B 17/32002 606/159 |
| 2004/0204671 A1 | 10/2004 | Stubbs et al. |
| 2005/0043690 A1 | 2/2005 | Todd |
| 2005/0085692 A1 | 4/2005 | Kiehn et al. |
| 2005/0277970 A1 | 12/2005 | Norman et al. |
| 2006/0036132 A1 | 2/2006 | Renner et al. |
| 2006/0047185 A1 | 3/2006 | Shener |
| 2006/0241586 A1 | 10/2006 | Wilk |
| 2008/0015621 A1 | 1/2008 | Emanuel |
| 2008/0058588 A1 | 3/2008 | Emanuel |
| 2008/0058842 A1 | 3/2008 | Emanuel |
| 2008/0097468 A1 | 4/2008 | Adams |
| 2008/0097469 A1 | 4/2008 | Gruber |
| 2008/0097470 A1 | 4/2008 | Gruber |
| 2008/0097471 A1 | 4/2008 | Adams |
| 2008/0135053 A1 | 6/2008 | Gruber |
| 2008/0146872 A1 | 6/2008 | Gruber |
| 2008/0146873 A1 | 6/2008 | Adams |
| 2008/0245371 A1 | 10/2008 | Gruber |
| 2008/0249366 A1 | 10/2008 | Gruber |
| 2008/0249534 A1 | 10/2008 | Gruber |
| 2008/0249553 A1 | 10/2008 | Gruber |
| 2008/0262308 A1 | 10/2008 | Prestezog |
| 2009/0082628 A1 | 3/2009 | Kucklick |
| 2009/0270812 A1 | 10/2009 | Litscher |
| 2009/0270895 A1 | 10/2009 | Churchill |
| 2009/0270896 A1 | 10/2009 | Sullivan |
| 2009/0270897 A1 | 10/2009 | Adams |
| 2009/0270898 A1 | 10/2009 | Chin |
| 2010/0087798 A1 | 4/2010 | Adams |
| 2010/0125287 A1 | 5/2010 | Cole et al. |
| 2010/0152647 A1 | 6/2010 | Shener |
| 2011/0166419 A1 | 7/2011 | Reif |
| 2012/0078038 A1 | 3/2012 | Sahney |
| 2012/0172889 A1 * | 7/2012 | Chin ............... A61B 17/32002 606/119 |
| 2013/0060270 A1 | 3/2013 | Teeslink et al. |
| 2013/0131452 A1 | 5/2013 | Kuroda |
| 2014/0031834 A1 | 1/2014 | Germain et al. |
| 2016/0206339 A1 | 7/2016 | Akilian et al. |

* cited by examiner

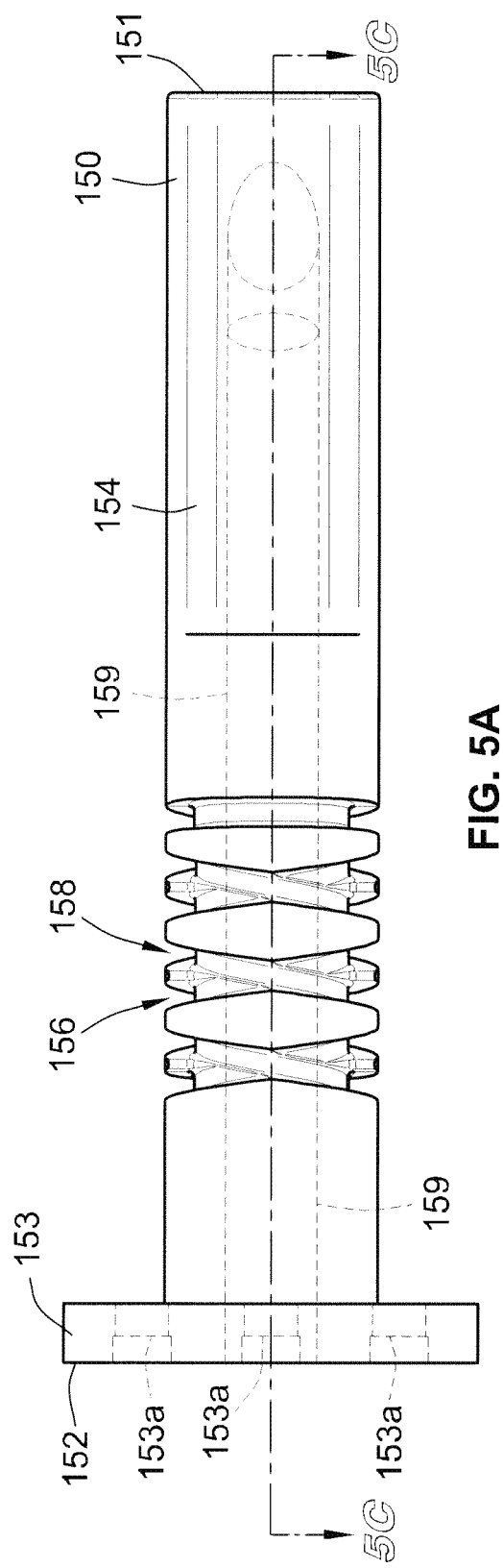
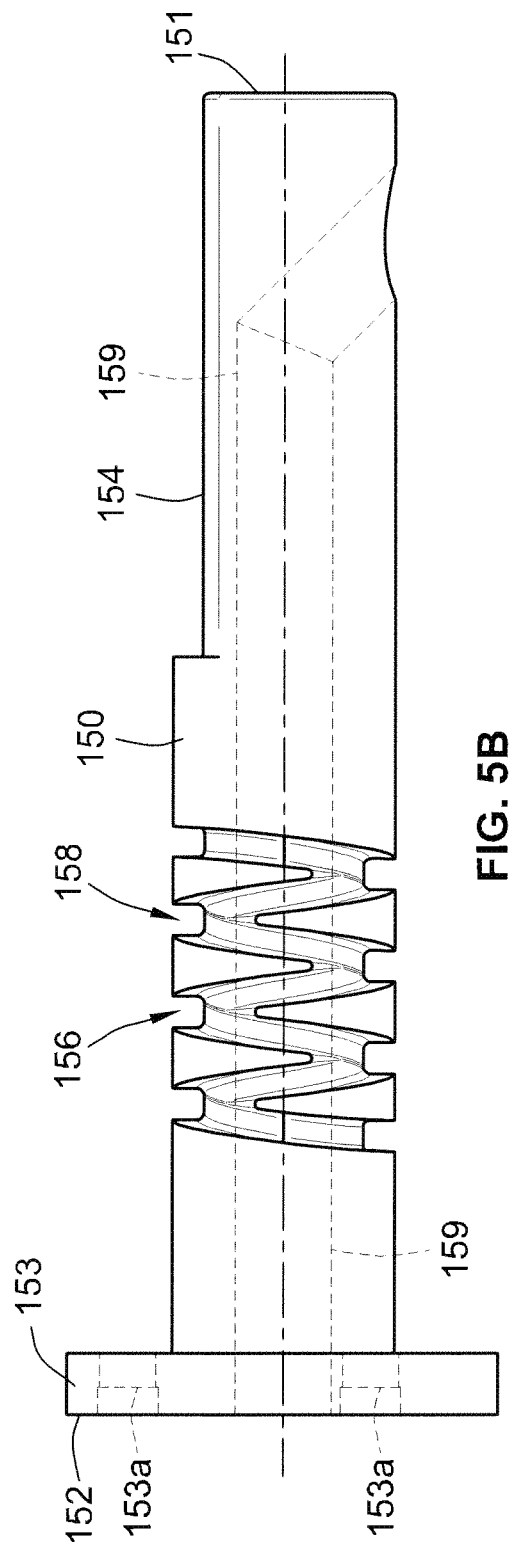
FIG. 5A
FIG. 5B

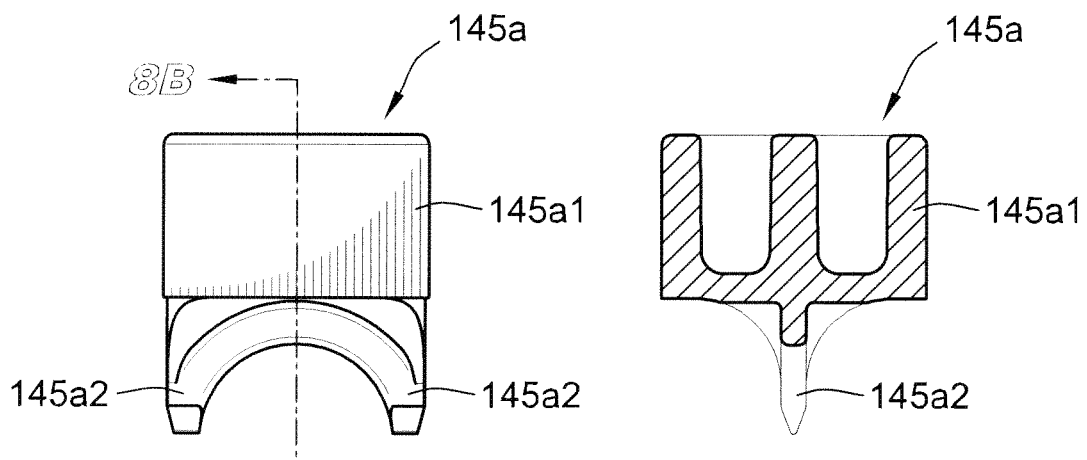
FIG. 8A
FIG. 8B
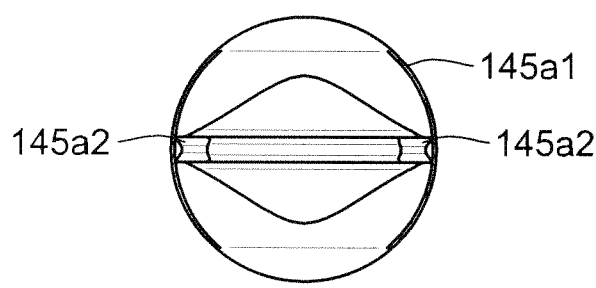
FIG. 8C
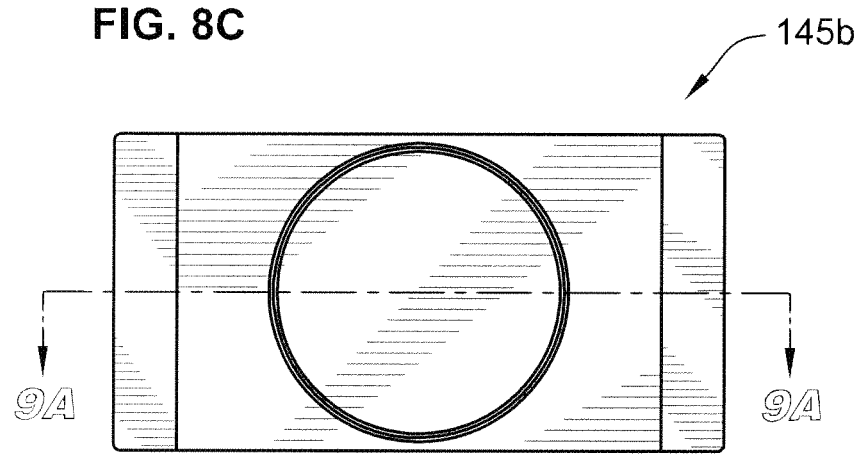
FIG. 9B
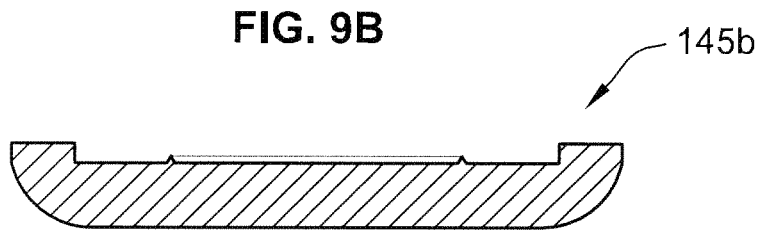
FIG. 9A

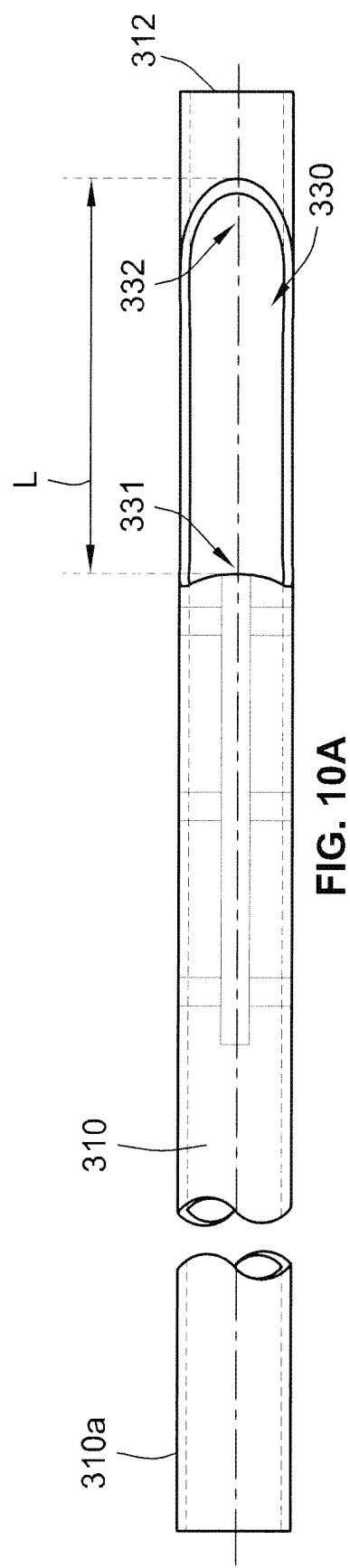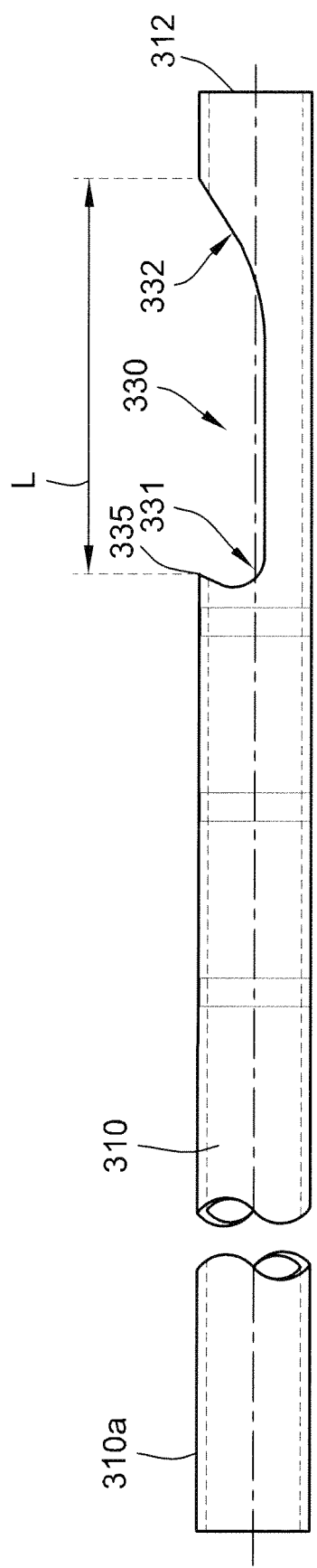

RECIPROCATING ROTARY SURGICAL CUTTING DEVICE AND SYSTEM FOR TISSUE RESECTING, AND METHOD FOR ITS USE

CROSS-REFERENCE TO RELATED APPLICATIONS

This application is a continuation of U.S. patent application Ser. No. 16/407,291, filed on May 9, 2019, which is a continuation of U.S. patent application Ser. No. 15/221,967, filed on Jul. 28, 2016 and now U.S. Pat. No. 10,299,819, the entire contents of each of which are hereby incorporated herein by reference.

FIELD OF THE INVENTION

The present disclosure generally relates to endoscopic tissue resecting systems, and more particularly, to a reciprocating rotary surgical instrument for cutting and detaching tissue that includes a planetary gear assembly to increase or decrease rotational speed.

BACKGROUND

Conventional surgical instruments that cut tissue generally include an outer tube and an inner member that rotates or translates axially within the outer tube. The outer tube and inner member may interact to create shear forces that cut tissue. In another variety of surgical instruments that cut tissue, the inner tube simultaneously rotates and translates axially within the outer tube. In the aforementioned prior art surgical instruments the inner tube rotates at approximately the same speed as the rotary driver.

SUMMARY

In one aspect, an endoscopic tissue resecting system includes a reciprocating rotary surgical instrument for cutting and detaching tissue that includes a planetary gear assembly to increase or decrease rotational speed.

According to some implementations, a rotary surgical instrument includes an endoscope and a resector. The resector includes a handpiece, a rotary driver (e.g. a motor), a drive assembly, and a cutting device (e.g., an elongated inner member and an elongated outer member). The rotary driver is positioned within the handpiece. The drive assembly may be positioned within the handpiece. The drive assembly is coupled at its distal end to the cutting device, and coupled at its proximal end to the rotary driver. The drive assembly is configured to cause the elongated inner member of the cutting device to rotate about an axis, move linearly along the axis in a first direction, switch directions, and move linearly back along the axis in a second direction opposite the first direction, etc. The cutting device is configured to cut and detach tissue during the rotation and the linear moving along the axis in the first direction. The drive assembly includes a helical member, a translation piece, and a planetary gear assembly. The helical member is coupled to the rotary driver (e.g., via a drive coupler and inner hub) and the planetary gear assembly. The planetary gear assembly is coupled to the cutting device. The translation piece is disposed in a groove of the helical member such that the rotary driving of the drive assembly results in the helical member moving linearly in the first direction, switching directions, moving linearly back in the second direction, switching directions back to the first direction, etc. This linear moving of the helical member occurs while the helical member is also rotating. The planetary gear assembly includes a fixed ring gear, one or more planet gears, and a sun gear. The fixed ring gear meshes with the planet gears, which in turn mesh with the sun gear. The sun gear is coupled to the elongated inner member of the cutting device such that rotary driving of the drive assembly results in the elongated inner member rotating at an increased or decreased speed relative to the rotary speed of the rotary driver.

In some implementations, the planetary gear assembly (e.g., an epicyclic gearing assembly) can include a number of possible configurations of a fixed gear (e.g., a ring gear), a follower (e.g., one or more planet gears), and a driver (e.g., a sun gear) to achieve the desired. In some instances, the speed of the follower is greater than the speed of the driver. In other instances, the speed of the follower is less than the speed of the driver. Yet in other instances, the speed of the follower is equal to the speed of the driver.

In one implementation, the planetary gear assembly includes a fixed ring gear, one or more planet gears (i.e., drivers) and a sun gear (i.e., follower). In another implementation, the planetary gear assembly includes a fixed sun gear, a ring gear (i.e., follower), and one or more planet gears (i.e., drivers). In yet another implementation, the planetary gear assembly includes a fixed ring gear, a sun gear (i.e., driver) and one or more planet gears (i.e., followers). In another implementation, the planetary gear assembly includes a ring gear (i.e., driver), a fixed sun gear, and one or more planet gears (i.e., followers).

In some implementations, the elongated inner member rotates at a rotary speed about two times, about three times, about four times, about five times, about ten times, etc. greater than a rotary speed of the rotary driver (e.g., the motor).

According to some implementations, the resector includes an inner hub and an outer hub. In such implementations, the inner hub is coupled (e.g., directly) to the rotary driver (e.g., a motor). The helical member is coupled to the inner hub and is located within the outer hub. The inner hub engages with the helical member, thereby coupling the helical member to the inner hub such that the helical member rotates with the inner hub while being free to translate (e.g., move linearly) relative to the inner hub. The helical member includes a helical groove configured to receive at least a portion of the translation piece therein. In some implementations, the helical groove includes a left-hand threaded helical channel, a right-hand threaded helical channel, or both. In some such implementations, the left-hand threaded helical channel and the right-hand threaded helical channel are blended at their ends to form a single continuous channel or groove. In some implementations, the translation piece includes a follower at least partially received within the helical groove and a sealing cap and/or clip positioned over the follower. The follower is free to swivel relative to the sealing cap. The follower has an arched bridge shape. The translation piece is coupled to the helical member such that the translation piece is at least partially disposed in the helical groove and swivels to follow the helical groove as the helical member rotates and reciprocates.

According to some implementations, the outer hub houses therein the helical member and the planetary gear assembly, which is comprised of the ring gear, the planet gears, the sun gear, and a planetary gear carrier. The planet gears are rotary supported to stub shafts of the planetary gear carrier, which is coupled to the helical member such that the planetary gear carrier rotates with the helical member and the rotary driver (e.g., the motor). The cutting device is coupled to the planetary gear assembly such that the elongated inner member of the cutting device rotates and moves linearly.

According to some implementations, the planetary gear assembly and helical member are not coupled. In some implementations, the planetary gear assembly and helical member may be housed in separate outer hubs.

According to some implementations, the elongated inner member of the cutting device includes an implement having a chamfered cutting edge at a distal end of the elongated inner member. In some implementations, the chamfered cutting edge is a straight cutting edge. Alternatively, the chamfered edge is an angled cutting edge.

According to some implementations, the cutting device includes an elongated outer member. In such implementations, the elongated inner member of the cutting device is received at least partially within the elongated outer member. The elongated outer member includes a cutting window disposed proximate to a tip of the elongated outer member. The cutting window is an opening in the elongated outer member configured to expose at least a portion of the elongated inner member to tissue. In some implementations, the cutting window has a U-shaped distal end and a saddle-shaped proximal end. The proximal or distal end of the cutting window can include a hook.

The details of one or more implementations of the present disclosure are set forth in the description below and the accompanying drawings. Other features will be apparent from the description and drawings, and from the claims.

BRIEF DESCRIPTION OF THE DRAWINGS

FIG. 5A is a bottom plan view of a helical member of the driving assembly of FIGS. 2A and 2B;

FIG. 5B is a side view of the helical member of FIG. 5A;

FIG. 8A is a front view of the follower of the driving assembly of FIGS. 2A and 2B;

FIG. 8B is a side cross-sectional view of the follower of FIG. 8A;

FIG. 8C is top plan view of the follower of FIG. 8A;

FIG. 9A is a top plan view of a cap of the driving assembly of FIGS. 2A and 2B;

FIG. 9B is side cross-sectional view of the cap of FIG. 9A;

FIG. 10A is a partial top plan view of an elongated outer member of the cutting device of the cutting device of FIGS. 2A and 2B;

FIG. 10B is a partial side view of the elongated outer member of FIG. 10A;

Figure 1:
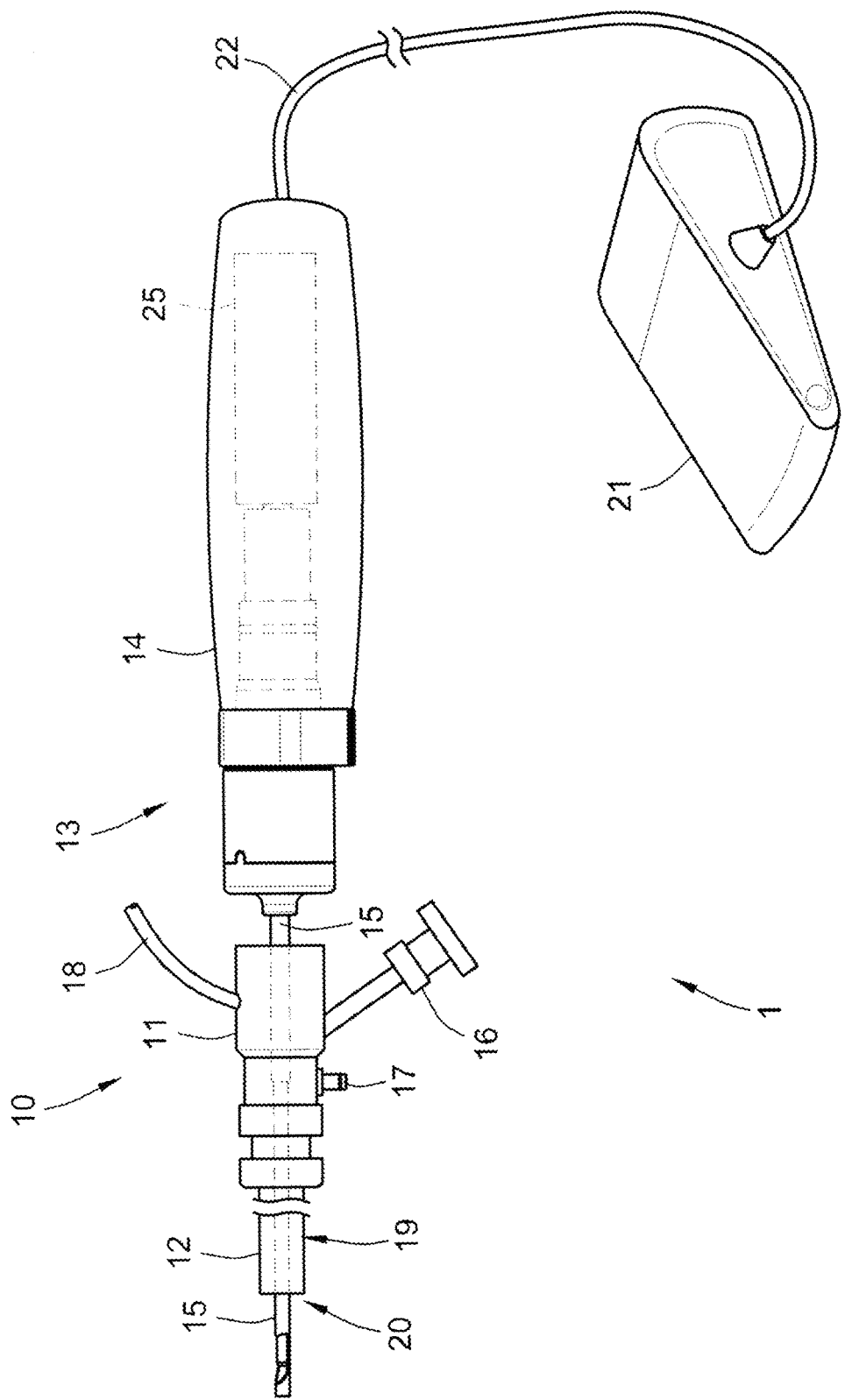
FIG. 1 is a perspective view of a tissue resecting system including an endoscope and a handpiece according to some implementations of the present disclosure.

While the present disclosure is susceptible to various modifications and alternative forms, specific implementations have been shown by way of example in the drawings and will herein be described in detail. It should be understood, however, that it is not intended to limit the present disclosure to the particular forms disclosed and illustrated, but on the contrary, the intention is to cover all modifications, equivalents, and alternatives falling within the spirit of the present disclosure.

DETAILED DESCRIPTION

Referring to FIG. 1, a tissue resecting system 1 includes an endoscope 10 (e.g., a hysteroscope) and a handpiece 14. The endoscope 10 includes an endoscope body 11 and an insert portion 12 that extends from the endoscope body 11 to a distal end of the endoscope 10. The insert portion 12 is insertable into an organ (e.g., a uterus, a prostate, a bladder, etc.) of a patient for use in a tissue resecting procedure in the organ. The handpiece 14 includes a rotary driver 25 (e.g., motor) and a resector 13. The handpiece 14 is received by the endoscope 10 to resect (e.g., cut, detach and remove) tissue from the organ.

The endoscope 10 may also include other devices for use when conducting a tissue resecting procedure. For example, the endoscope 10 includes an observation port 16 configured to be coupled to a camera (not shown) and a light port 17 configured to be coupled to an illumination source (not shown). Together, the camera and the illumination source allow the operator to visualize and capture images from an area around the distal end of the endoscope 10. It is understood, however, that the endoscope 10 is shown as an example, and that other similar devices (with fewer or more features) can be employed according to aspects of the present disclosure (e.g., to accommodate the resector 13).

In some implementations, the endoscope 10 includes an inlet port 18 that receives fluid (e.g., saline, sorbitol, glycine, etc.) into the endoscope 10. An inflow passageway 19 is formed in the endoscope 10 and extends from the inlet port 18 to an inflow opening 20 at the distal end of the endoscope 10. The fluid flows from a fluid source (not shown), through the inlet port 18, then the inflow passageway 19, and then out of the inflow opening 20, and into the organ at the distal end of the endoscope 10.

As shown in FIG. 1, the tissue resecting system 1 may include a footswitch 21 that activates and/or controls aspects of the handpiece 14. For example, the footswitch 21 can be coupled to the handpiece 14, via a flexible drive shaft 22, to drive a pump (not shown) and/or to drive a cutting device 15 of the resector 13. The tissue resecting system 1 may include a control unit (not shown) that activates and/or controls aspects of the handpiece 14. For example, the control unit can be coupled to the handpiece 14, via a cable, to drive the cutting device 15 of the resector 13.

Figure 2A:
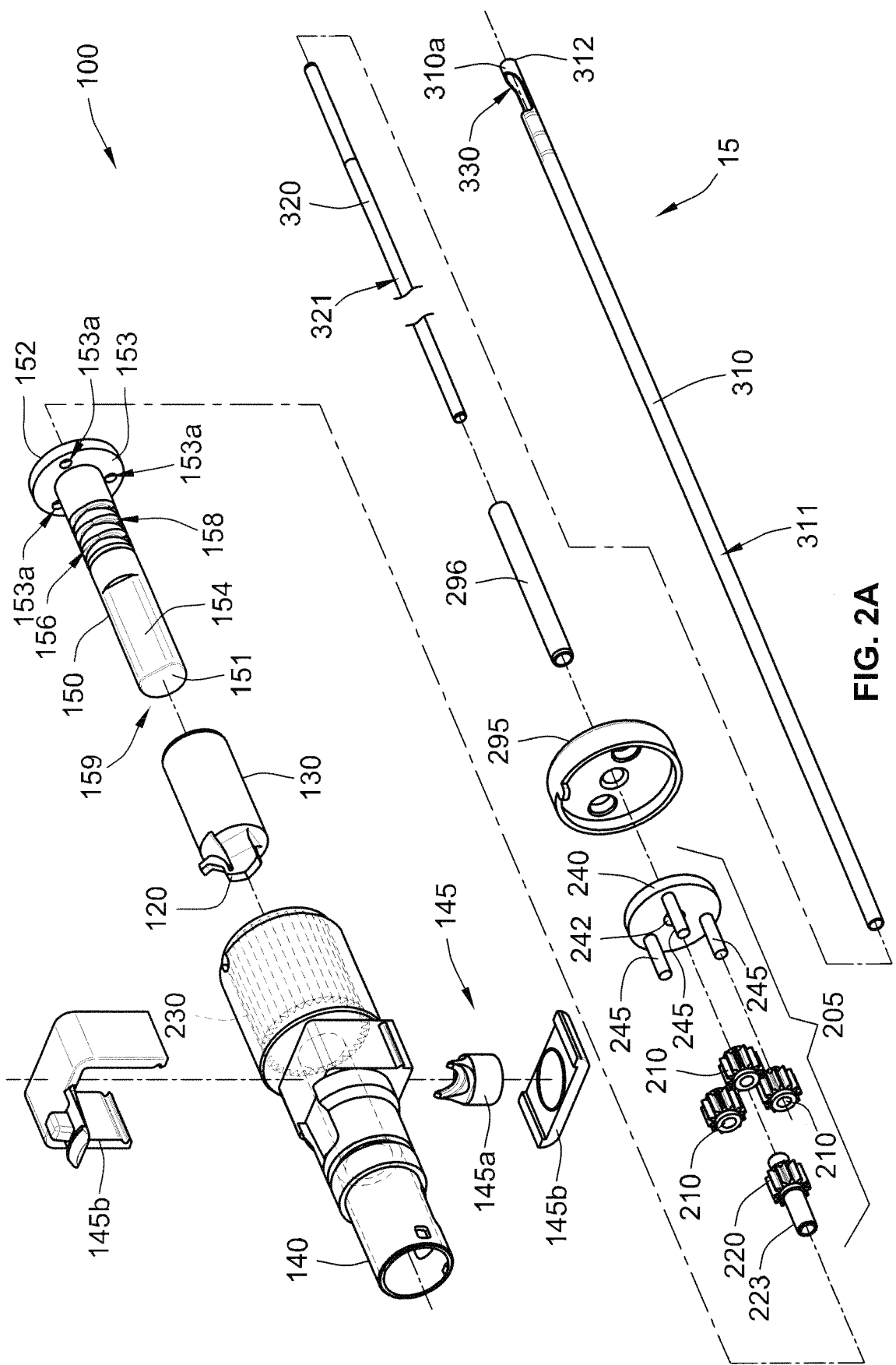
FIG. 2A is an exploded perspective view of a resector of FIG. 1, including a drive assembly and a cutting device.
Figure 2B:
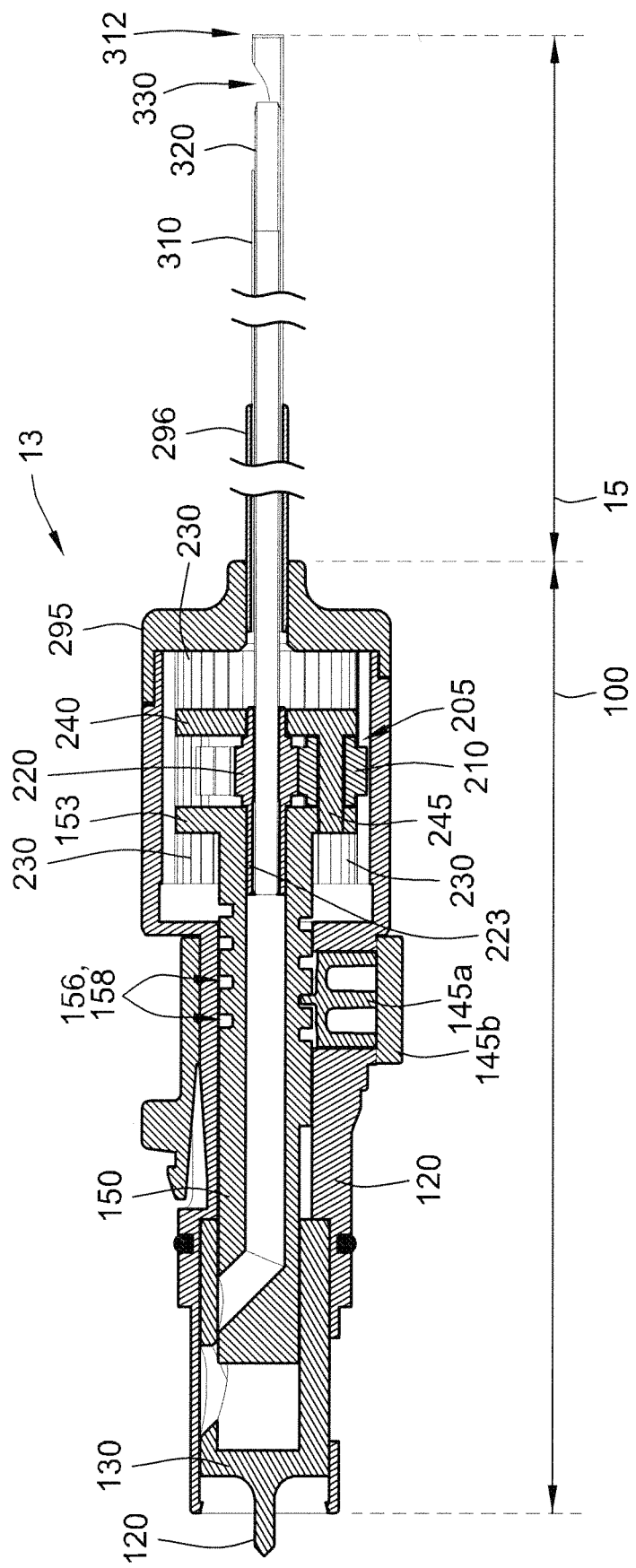
FIG. 2B is a partial assembled cross-sectional side view of the resector of FIG. 2A.

As shown in FIGS. 2A and 2B, the resector 13 includes the cutting device 15 and a driving assembly 100. The driving assembly 100 includes an inner hub 130, an outer hub 140, a translation piece 145, a helical member 150, and a planetary gear assembly 205. The handpiece 14 is disposed at a proximal end of the endoscope body 11. The cutting device 15 of the resector 13 extends from the handpiece 14 and passes correspondingly through the endoscope body 11 and the endoscope insert portion 12. At least a portion of the cutting device 15 is disposed beyond the distal end of the endoscope insert portion 12 to access tissue in the organ.

The cutting device 15 includes an elongated outer member 310 and an elongated inner member 320 that performs tissue resection. The elongated outer member 310 is tubular with a hollow interior or lumen 311 (FIG. 2A). The elongated inner member 320 is tubular with a hollow interior or lumen 321 (FIG. 2A). As shown in FIG. 2B, the elongated inner member 320 is at least partially received inside the hollow interior or lumen 311 of the elongated outer member 310. In some implementations the elongated outer member 310 is attached (e.g., fixed) to the outer hub 140 via a cap 295 and/or a supporting tube 296 and does not move relative thereto. The elongated outer member 310 includes a tip 312, which is blunt (e.g., the corners are rounded). The distal end of the outer member 310 defines a cutting window 330 through a wall 310a of the outer member 310. The size (e.g., an inner diameter or an outer diameter) of outer member 310 is about 3 mm. In another embodiment, the size of the outer member 310 is about 2 mm. In another embodiment, the size of the outer member 310 is about 4 mm. For example, the size (e.g., an inner diameter or an outer diameter) of the outer member can be from about 1 mm to about 5 mm or from about 2 mm to about 4 mm. The elongated outer member 310 is sized such that it can receive the elongated inner member 320.

The inner hub 130 of the driving assembly 100 includes a drive coupler 120. In some implementations, when the drive assembly 100 is positioned within the handpiece 14, the drive coupler 120 couples and/or mounts to the rotary driver 25 positioned in the handpiece 14. The rotary driver 25 (FIG. 1) turns the drive coupler 120 causing the inner hub 130 and the helical member 150 to rotate about an axis (e.g., a central axis of the inner hub 130 and/or the helical member 150). The helical member 150 and the translation piece 145 are coupled together such that rotation of the helical member 150 causes linear movement of the helical member 150, as described further below.

As best shown in FIG. 2B, the proximal end 151 of the helical member 150 is located within the inner hub 130 and the outer hub 140 during operation of the resector 13. In some implementations, the distal end 152 of the helical member 150 includes a platen 153 that is located within the outer hub 140 during operation of the resector 13. In some implementations, the platen 153 forms a multitude of receiving openings 153a configured to mate with a portion of the planetary gear assembly 205. In some implementations, the platen 153 is a separate component, coupled to the helical member 150.

As best shown in FIGS. 2A and 2B, the planetary gear assembly 205 includes a fixed ring gear 230, planet gears 210, a sun gear 220, a lumen 223, a planetary gear carrier 240, stub shafts 245, and platen 153. As best shown in FIG. 3B, the outer hub 140 includes a fixed ring gear 230 that meshes with the planet gears 210, which then mesh with the sun gear 220. The sun gear 220 is rotationally fixed to the lumen 223 (FIG. 2A), which is coupled to the elongated inner member 320 (FIG. 3A) such that rotation of the sun gear 220 and the lumen 223 at a first rotational speed causes rotation of elongated inner member 320 at the first rotational speed, which is increased or decreased relative to a second rotational speed of the rotary driver 25 (e.g., motor). The increased or decreased relative rotational speed is caused by the size and relationship between the fixed ring gear 230, and the sun gear 220.

The stub shafts 245 extend between the planetary gear carrier 240 and the platen 153. In some implementations, the stub shafts 245 are received in the receiving openings 153a of the platen 153. The stub shafts 245 support the planet gears 210 in a rotational coupling such that each of the planet gears 210 can rotate about its respective stub shaft 245. The planetary gear carrier 240 forms an opening 242 (FIGS. 2A and 3A) therethrough to permit the lumen 223 and/or a portion of the elongated inner member 320 to pass therethrough without significantly impacting rotation of the lumen 223 and/or the elongated inner member 320. In some implementations, the opening 242 acts as a bearing surface for the lumen 223 to rotate.

Figure 3A:
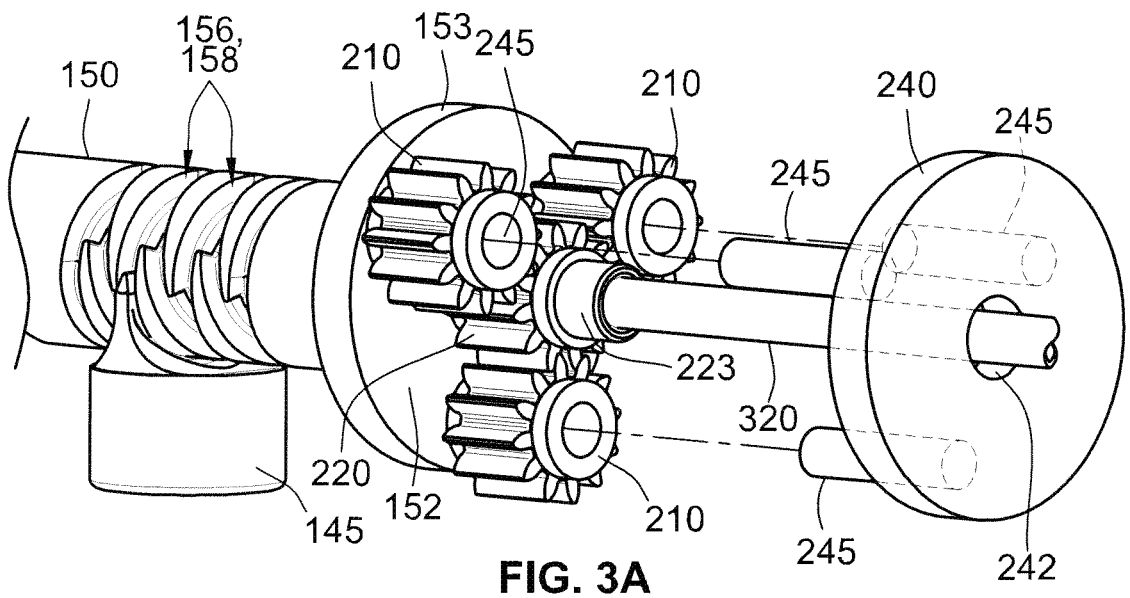
FIG. 3A is a partially exploded perspective view of a driving assembly of the resector of FIGS. 2A and 2B.
Figure 3B:
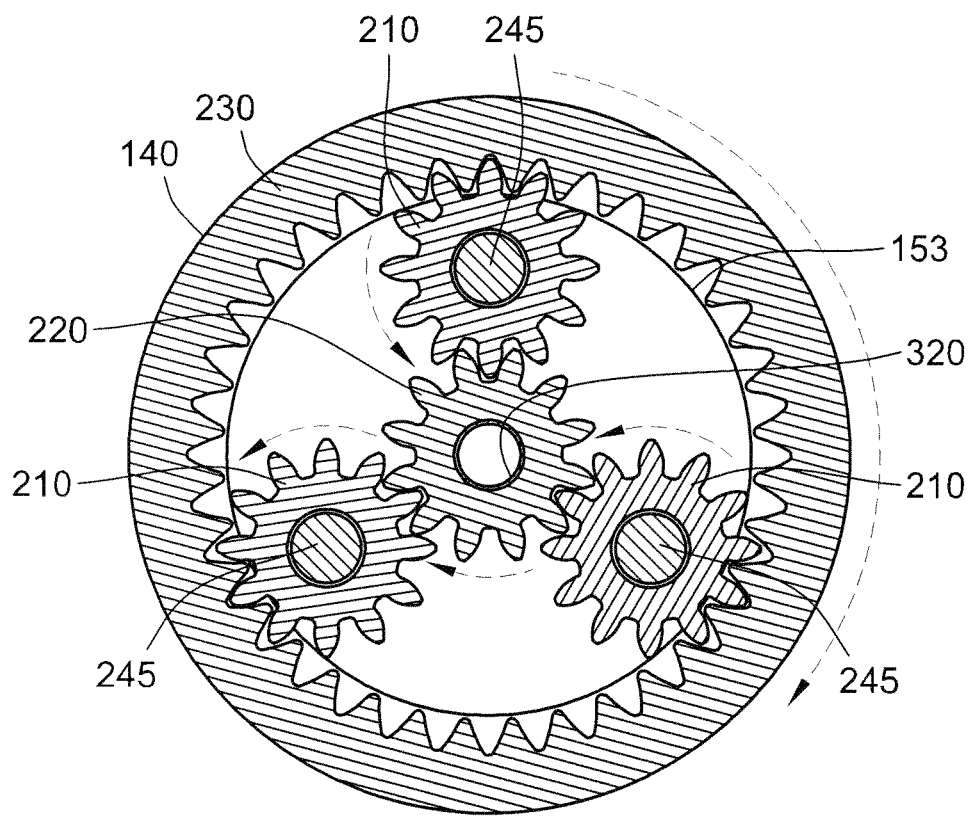
FIG. 3B is a partial cross-sectional view of a planetary gear assembly of the driving assembly of FIGS. 2A and 2B.

With reference to FIGS. 3A and 3B, when the planetary gear assembly 205 is assembled and positioned within the outer hub 140, the sun gear 220 is positioned to mesh with the planet gears 210, which in turn mesh with the fixed ring gear 230. As such, rotation of the helical member 150 about its central axis causes the platen 153 to rotate about the same central axis, which causes the planetary gear carrier 240 and the coupled stub shafts 245 to rotate about the same central axis. As the stub shafts 245 rotate about the central axis of the helical member 150, the planet gears 210 (rotationally mounted to the stub shafts 245) and mesh with the fixed ring gear 230, thereby causing each planet gear 210 to rotate about its respective central axis and about its respective stub shaft 245. As the planet gears 210 are meshed with the sun gear 220, such rotation of the planet gears 210 causes the sun gear 220 to rotate about its central axis, which coincides with the central axis of the helical member 150.

Figure 3C:
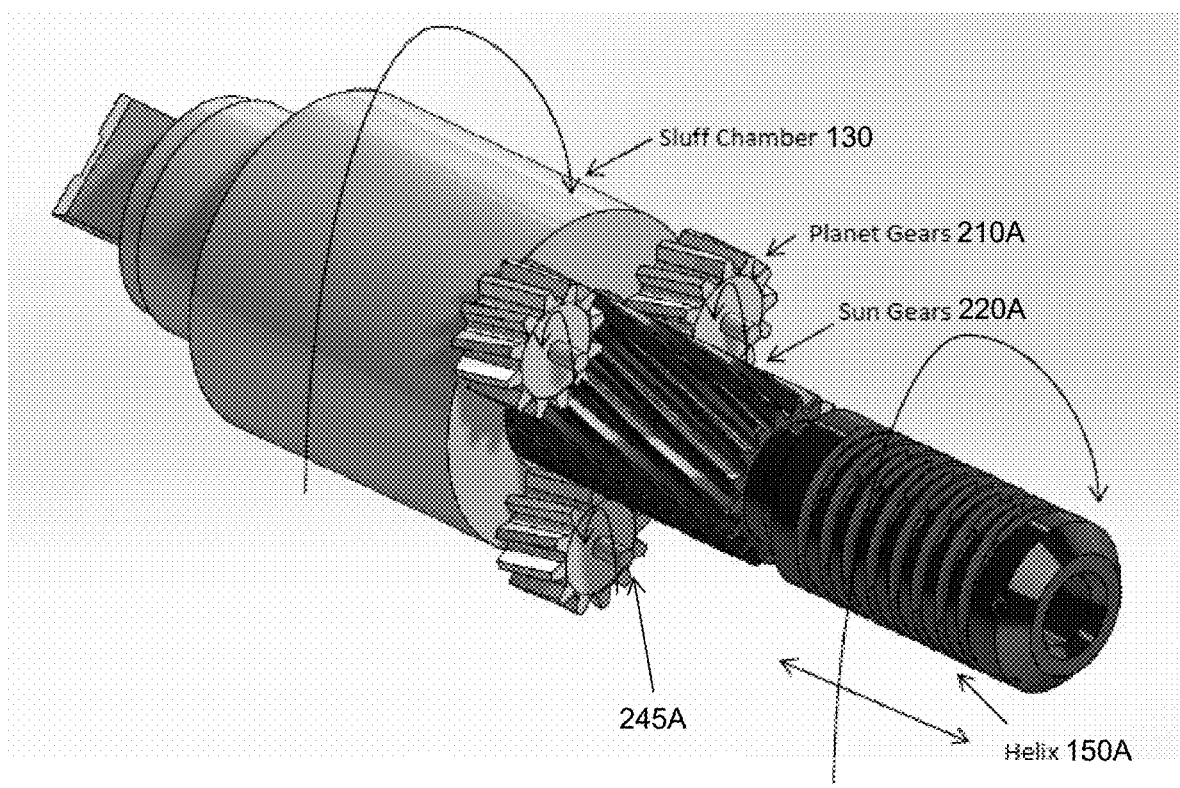
FIG. 3C is a perspective view of a planetary gear assembly of a resector in accordance with another embodiment.

Referring to FIG. 3C, planetary gear assembly 205A is positioned within outer hub 140A. Sun gear 220A is positioned to mesh with planet gears 210A, which in turn mesh with the fixed internal ring gear (not shown). Planet gears 210A are connected to sluff chamber 130 (i.e., an inner hub) via stub shafts 245A. As the stub shafts 245A rotate about the central axis of the helical member 150A, the planet gears 210A (rotationally mounted to the stub shafts 245A) and mesh with the fixed ring gear 230A, thereby causing each planet gear 210A to rotate about its respective central axis and about its respective stub shaft 245A. As the planet gears 210A are meshed with the sun gear 220A, such rotation of the planet gears 210A causes the sun gear 220A to rotate about its central axis, which is part of helical member 150A. As such, rotation of sun gear 220A about its central axis causes the helical member 150A to rotate about the same central axis. A follower (not shown) allows the helical member 150A to move laterally in both directions, along the axis of rotation.

Figure 3D:
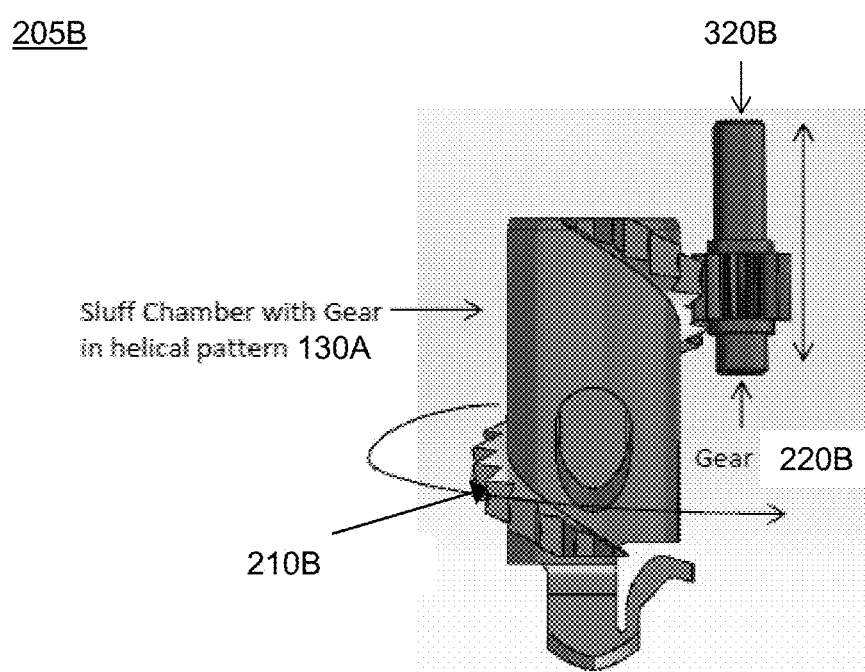
FIG. 3D is a perspective view of a driving assembly of a resector in accordance with another embodiment.
Figure 4D:
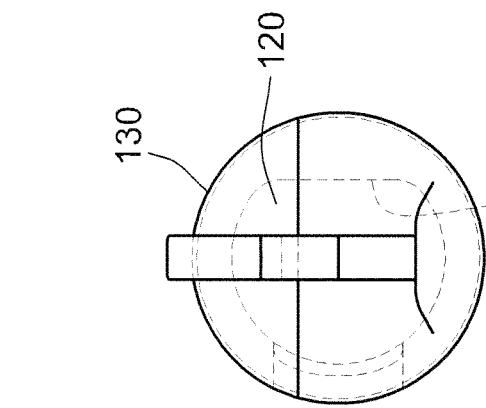
FIG. 4D is front view of the inner hub of FIG. 4A.
Figure 4A:
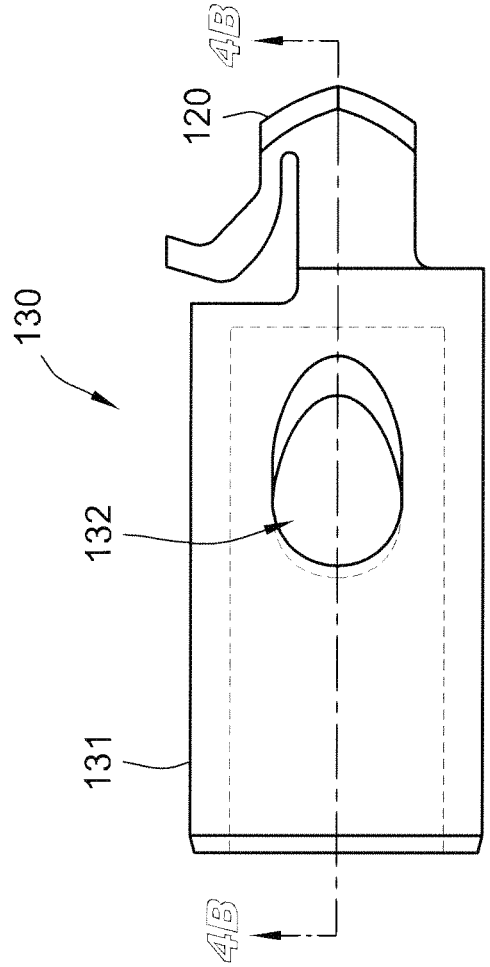
FIG. 4A is a top plan view of an inner hub of the driving assembly of FIGS. 2A and 2B.
Figure 4C:
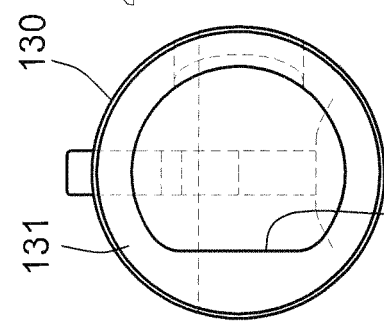
FIG. 4C is a rear view of the inner hub of FIG. 4A.
Figure 4B:
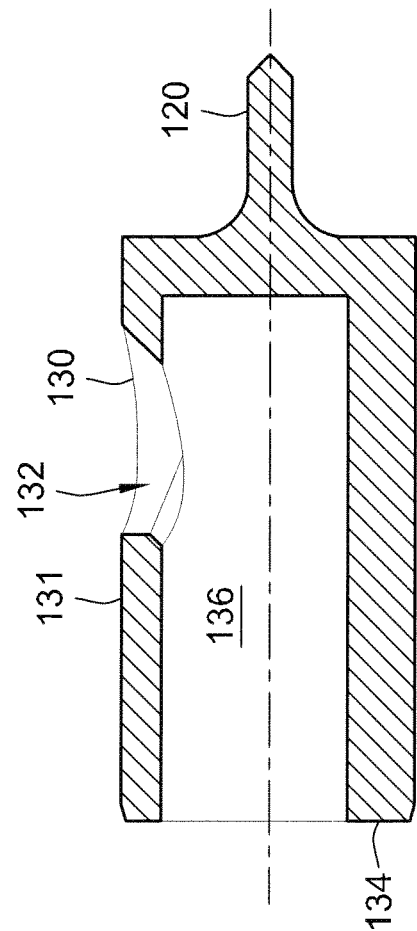
FIG. 4B is a cross-sectional side view of the inner hub of FIG. 4A.

Referring to FIG. 3D, planetary gear assembly 205B has a sluff chamber 130A (i.e., an inner hub) and a sun gear 220B. A helical gear 210B is formed on the sluff chamber 130A. The pattern on helical gear 210B can be a reversing basis such that axial motion (e.g., lateral movement) of the sun gear 220B connected to inner member 320B. A wall (not shown) at the proximal and distal ends of the sluff chamber can assist the sun gear 220B to move along the helical gear 210B on sluff chamber 130A. Other mechanisms, such as a cam, could be implemented in the driving assemblies described herein to create axial motion.

Referring to FIGS. 4A-4D, the inner hub 130 includes the drive coupler 120, a lumen 136, an aspiration opening 132, and a flat or key 134. The drive coupler 120 extends from the proximal end of the inner hub 130 and mounts in the rotary driver 25. Debris from the cutting device 15 is aspirated through the aspiration opening 132. The flat 134 is coupled with a corresponding feature or flat 154 of the helical member 150 (FIG. 5B) so that rotation of the inner hub 130 causes the helical member 150 to rotate while allowing the helical member 150 to move axially relative to the inner hub 130 (e.g., the non-rotational feature 154 slides axially along/ against the non-rotational feature 134).

Figure 5C:
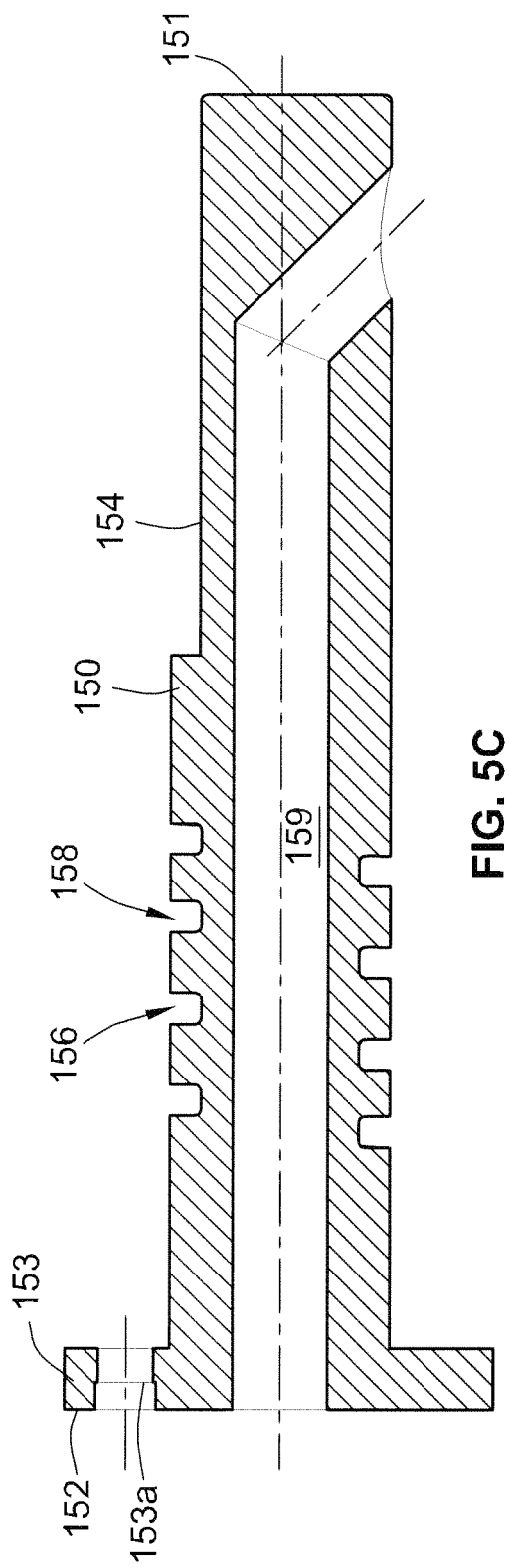
FIG. 5C is a cross-sectional side view of the helical member of FIG. 5B.
Figure 5D:
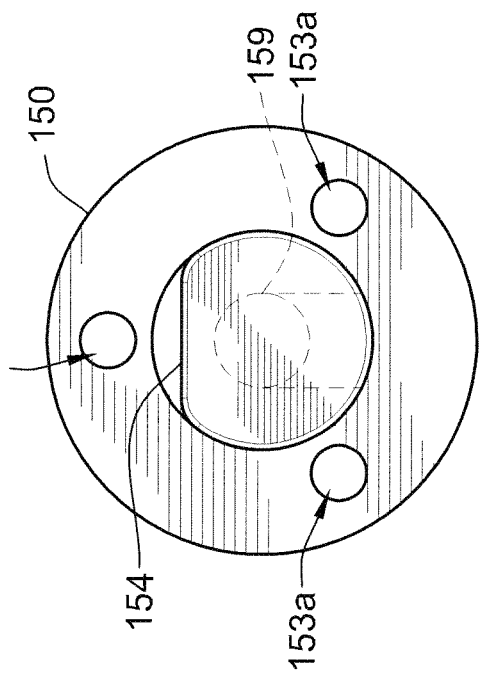
FIG. 5D is a front view of the helical member of FIG. 5A.

Referring to FIGS. 5A-5D, the helical member 150 of the driving assembly 100 is formed in a generally tubular shape with a through lumen 159. The helical member 150 includes the non-rotational feature 154, two helical channels 156, 158 disposed thereon, and the platen 153 located at the distal end 152. In some implementations, the platen 153 is a separate component, coupled to the helical member 150. As shown in FIG. 5B, the flat 154 is located near the proximal end 151 of the helical member 150 to engage with the corresponding feature 134 of the inner hub 130.

The two helical channels 156, 158 are disposed on a distal portion of the exterior surface of the helical member 150. One helical channel 156 is right-hand threaded; the other helical channel 158 is left-hand threaded. The pitch of each of the helical channels 156, 158 may be constant and/or variable, and each of the helical channels 156, 158 may have the same, or similar, pitch, or different pitches. In some implementations where the pitches of the helical channels 156, 158 are different, the helical member 150 is configured to move linearly in a first direction generally at a first linear speed and further configured to move linearly in a second opposite direction generally at a second linear speed that is different from the first linear speed. The helical channels 156, 158 are smoothly blended together at their ends to form a continuous groove so that there is a smooth transition from one helical channel to the other helical channel.

Figure 5E:
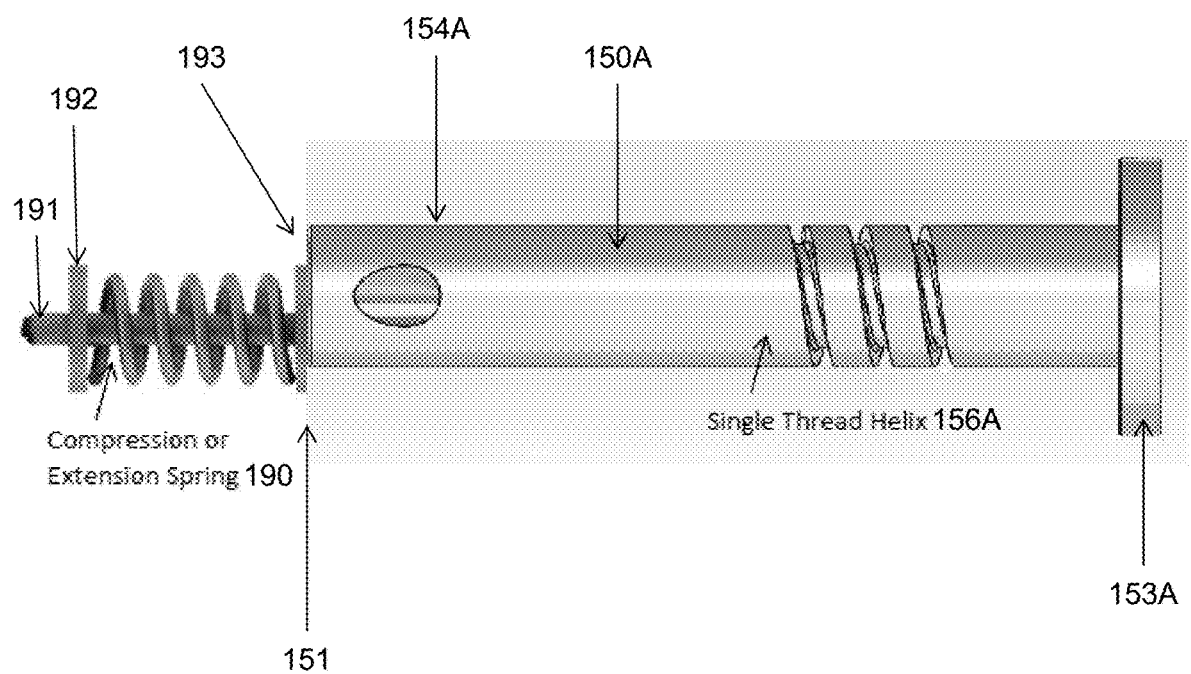
FIG. 5E is a side view of a helical member in accordance with an another embodiment of a driving assembly.

Referring to FIG. 5E, in an alternative implementation, the helical member 150A is formed in a generally tubular shape with a through lumen 159A. The helical member 150A includes the rotational feature 154A, one helical channel 156A disposed thereon, and the platen 153A located at the distal end 152. In some implementations, the platen 153A is a separate component, coupled to the helical member 150A. As shown in FIG. 5E, the rotational feature 154A is located near the proximal end 151 of the helical member 150A to engage with the corresponding feature 134 of the inner hub 130. Rotational feature 154A is essentially a helix with a one helical cut. This is an alternative embodiment to a dual pitch helical cuts embodiment.

The helical member also includes a spring 190. Spring 190 is disposed on spring mount 191 having a distal end and a proximal end. The spring 190 allows for quicker retraction of the cutting tube. At the distal end and the proximal end of the spring mount 191 are spring stops 192, 193. The helical member 150A with spring 190 can retract the helical member 150A and the elongated inner member 320 after cutting has occurred.

The follower (not shown) in this embodiment can be a ball follower that can ride in the helical groove as the tube cuts through tissue but allows the helix to quickly retract by allowing the ball follower to ride in an axial groove that connects the start and end points of the helical cut.

Figure 6A:
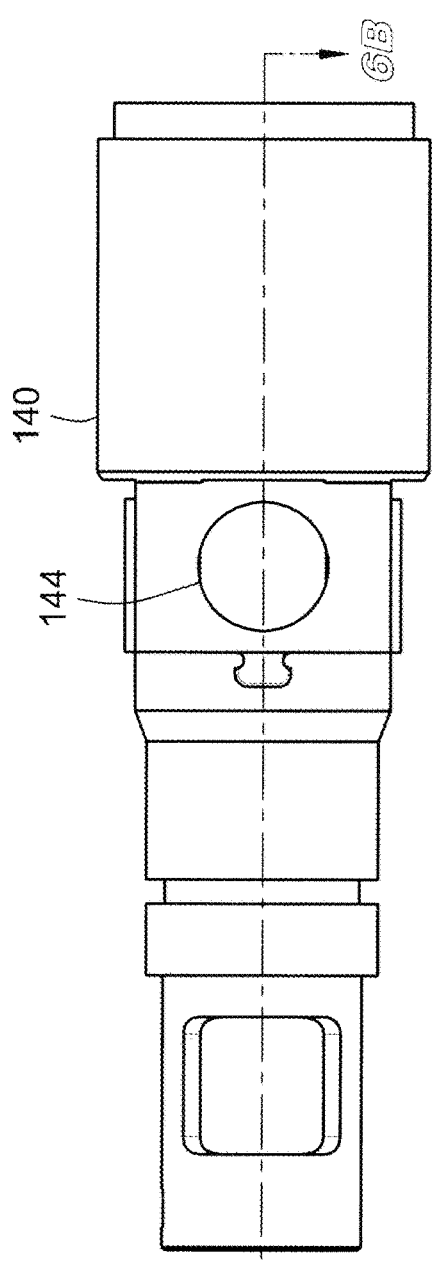
FIG. 6A is bottom plan view of the outer drive hub of the driving assembly of FIGS. 2A and 2B.
Figure 6C:
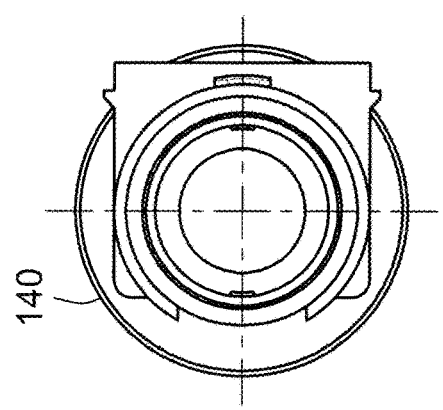
FIG. 6C is a front view of the outer drive hub of FIG. 6A.
Figure 6B:
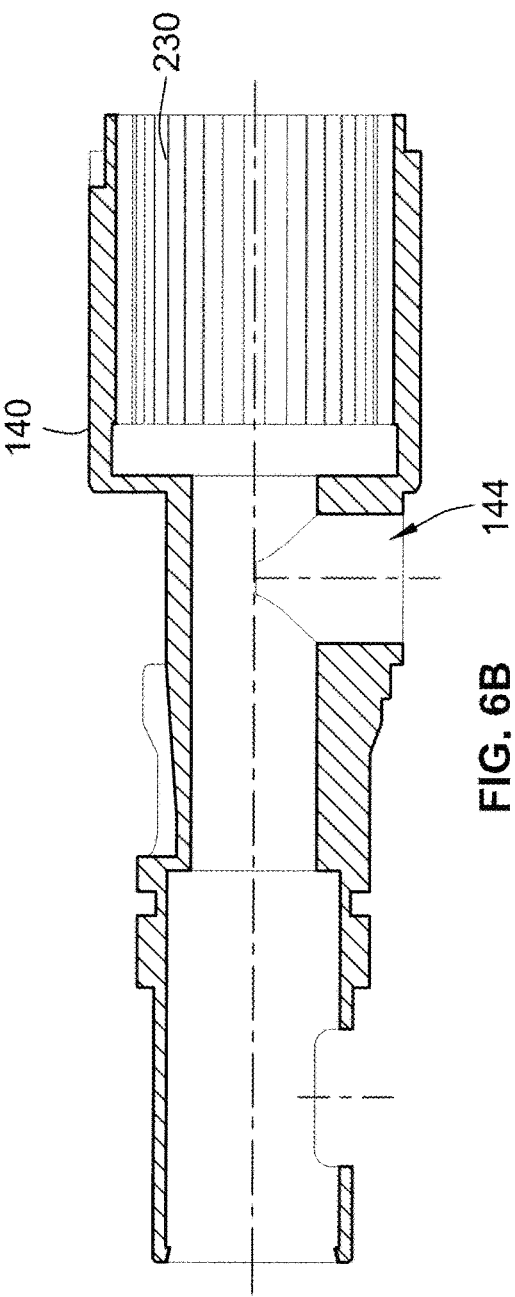
FIG. 6B is a cross-sectional side view of the outer drive hub of FIG. 6A.

Referring to FIGS. 6A-6C, the outer hub 140 of the driving assembly 100 does not move relative to the handpiece 14. The outer hub 140 encompasses the helical member 150, the follower 145a, the planetary gear assembly 205 and part of or the entirety of the inner hub 130. Referring back to FIGS. 2A and 2B, the outer hub 140 is formed of hard plastic and does not move relative to the handpiece 14. The outer hub 140 is molded as a single monolithic component as shown in FIG. 2A; however, in some alternative implementations, the outer drive hub 140 comprises two or more individual parts coupled together (e.g., two parts, three parts, etc.). During operation of the resector 13, the outer hub 140 houses therein the platen 153, the fixed ring gear 230, the planet gears 210 (two or more in number), the sun gear 220, and the planetary gear carrier 240. As shown, the fixed ring gear 230 is formed integrally with the outer drive hub 140 by molding it into the outer drive hub 140. Alternatively, the fixed ring gear 230 can be a separate component that is coupled to the outer drive hub 140. While three planet gears 210 are illustrated, any number of planet gears 210 can be included in the planetary gear assembly 205, such as, for example, one, two, three, four, five, etc.

Figure 7A:
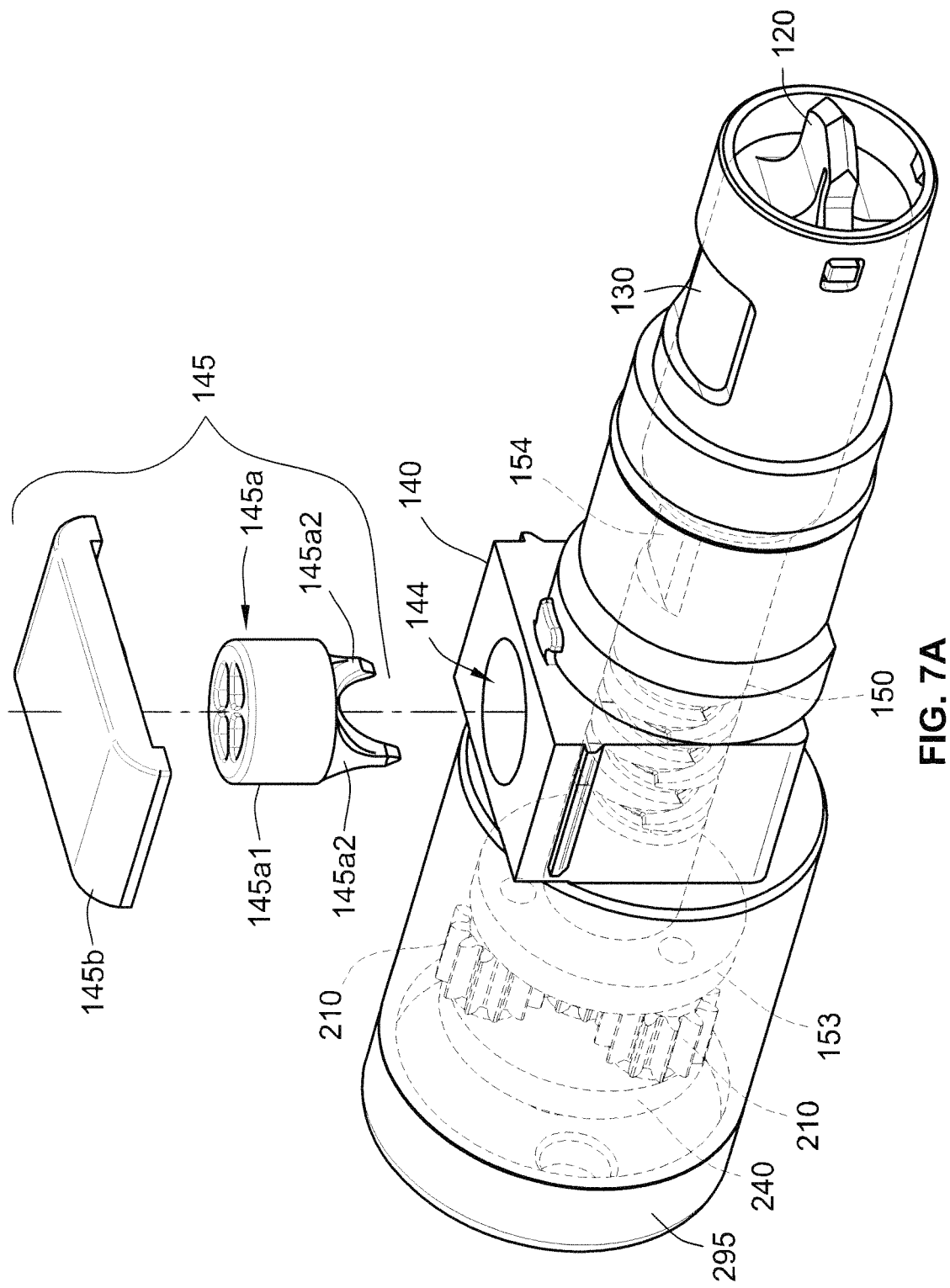
FIG. 7A is a partially exploded perspective view of the driving assembly of FIGS. 2A and 2B.

Referring to FIG. 7A, the follower 145a works in conjunction with the helical member 150, which includes the two helical channels 156, 158 and the flats 134, 154 that couple the inner hub 130 and the helical member 150 in a non-rotational fashion (e.g., the inner hub 130 and the helical member 150 do not rotate relative to one another), the rotary driver 25 only needs to rotate in one direction and does not require reversal of its rotational direction upon the follower 145a reaching the end of one of the helical channels 156, 158. Referring to FIGS. 9A and 9B, the cap 145b of the translation piece 145 covers the follower 145a to provide a seal to allow sufficient suction to remove aspirated debris. Also, the cap 145b is a separate piece from the follower 145a in order to allow the follower 145a to swivel (e.g., rotate) relative to the cap 145b.

Figure 7B:
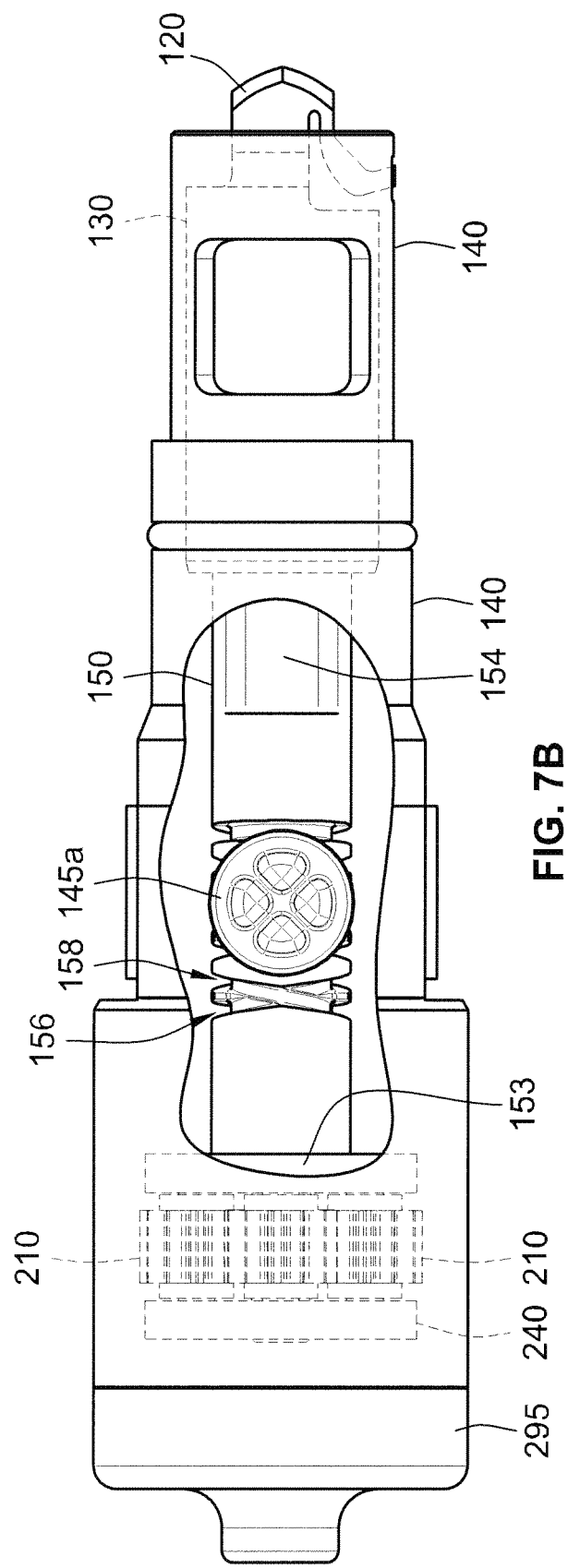
FIG. 7B is an assembled, partial bottom plan view of the driving assembly of FIG. 7A
Figure 7C:
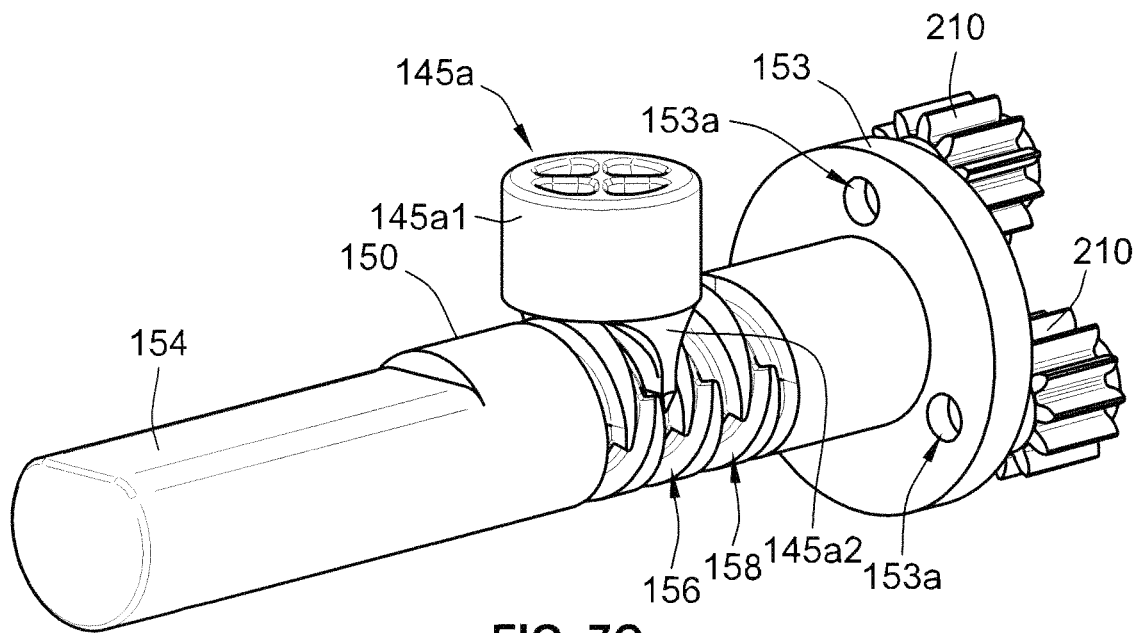
FIG. 7C is a perspective view of a follower of the driving assembly of FIGS. 2A and 2B engaging a first helical channel.
Figure 7D:
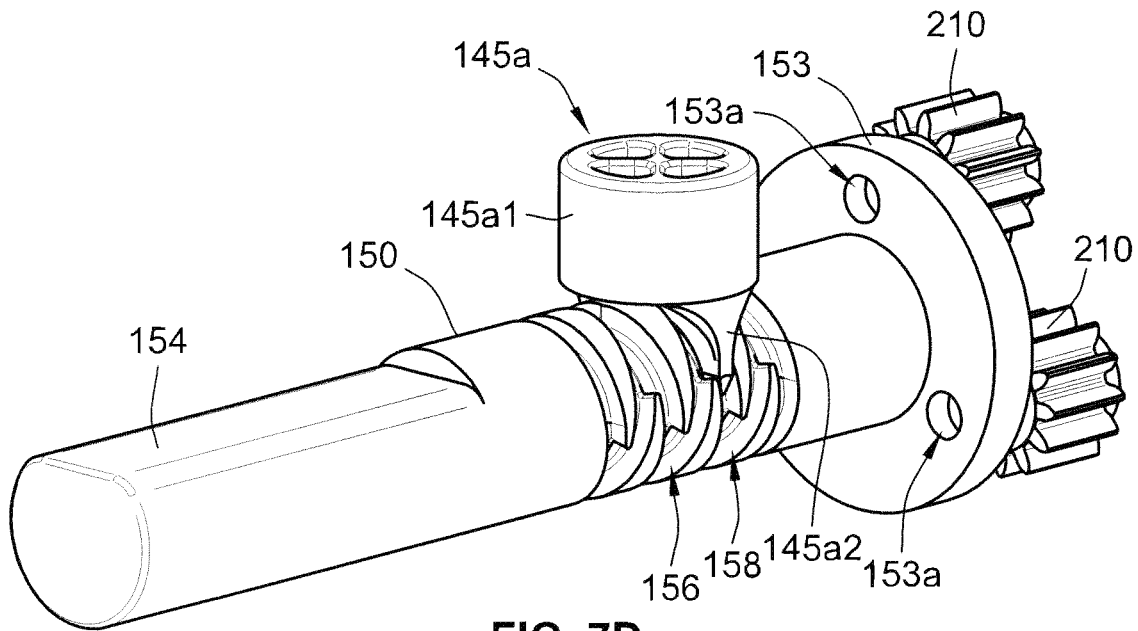
FIG. 7D is a perspective view of the follower engaging a second helical channel.

Referring to FIGS. 8A-8C, the follower 145a includes a cylindrical head 145a1 and two legs 145a2. As shown in FIGS. 7B-7D, the legs 145a2 form an arch and rest in the helical channels 156, 158 formed in the distal portion of the exterior surface of the helical member 150. The arch of the legs 145a2 is dimensionally related to the diameter described by the helical channels 156, 158 of the helical member 150.

Referring particularly to FIGS. 7C and 7D, as the helical member 150 and the inner hub 130 are mechanically driven by the rotary driver 25, the follower 145a (FIGS. 8A and 8B) follows the helical channels 156, 158, swiveling as the follower 145a smoothly transitions from helical channel 156 to helical channel 158 at the end of the distal portion of the helical member 150 having the helical channels 156, 158. The coupling of the follower 145a to the helical channels 156, 158 causes the helical member 150 to move linearly. Thus, the elongated inner member 320 of the cutting device 15, which is coupled to the helical member 150 via the planetary gear assembly 205 and the platen 153, also rotates and moves linearly to cut, detach and remove tissue.

The planetary gear carrier 240 is formed with the opening 242 at its approximate center. The sun gear 220 is formed in a tubular shape with the through lumen 223. The elongated inner member 320 is disposed within the distal end of the sun gear 220 and fixed therein, for example, by epoxy, injection-molded, or welding or over-molded plastic such that the elongated inner member 320 does not move relative to the sun gear 220 and/or the lumen 223. The proximal end of the lumen 223 of the sun gear 220 is fluidly coupled to the lumen 159 of the helical member 150, such that the sun gear 220 rotates freely from the helical member 150, but fluid and/or tissue can be aspirated through the lumen 223 of the sun gear 220 and to the lumen 159 of the helical member 150. The elongated outer member 310 is coupled to the cap 295 and/or the supporting tube 296 located near the distal end of the outer drive hub 140, and may be fixed thereto using, for example, epoxy, glue, an insert molding, overmolding, etc.

According to some implementations of the present disclosure, during operation of the tissue resecting system 1, the rotary driver 25 of the handpiece 14 turns the drive coupler 120 causing the inner hub 130, the helical member 150, and the planetary gear carrier 240 to rotate at the same first rotational speed or at the same first rpm (e.g., a first number of revolutions per minute). As described herein, the rotation of the planetary gear carrier 240 causes the planet gears 210 to mesh with the fixed ring gear 230 and rotate about the stub shafts 245 at a second rpm that is greater or less than the first rpm of the rotary driver 25, the inner hub 130, the helical member 150, and the planetary gear carrier 240. As each planet gear 210 rotates, it meshes with the sun gear 220, causing the sun gear 220 and the elongated inner member 320 to rotate at a third rpm that is greater or less than the second rpm.

According to some implementations, the rotary driver 25 operates at about 2,500 rpm and the planetary gear assembly 205 has a gearing ratio of about 4:1. In such implementations, the sun gear 220 and the elongated inner member 320 operate at about 10,000 rpm. According to some other implementations, the rotary driver 25 operates at about 1,000 rpm and the planetary gear assembly 205 has a gearing ratio of about 4:1. In such implementations, the sun gear 220 and the elongated inner member 320 operate at about 4,000 rpm. According to yet some other implementations, the rotary driver 25 operates at about 1,000 rpm and the planetary gear assembly 205 has a gearing ratio of about 10:1. In such implementations, the sun gear 220 and the elongated inner member 320 operate at about 10,000 rpm.

According to yet some further implementations, the rotary driver 25 operates at about 10,000 rpm and the planetary gear assembly 205 has a gearing ratio of about 1:4. In such implementations, the sun gear 220 and the elongated inner member 320 operate at about 2,500 rpm. According to yet some further implementations, the rotary driver 25 operates at about 10,000 rpm and the planetary gear assembly 205 has a gearing ratio of about 1:10. In such implementations, the sun gear 220 and the elongated inner member 320 operate at about 1,000 rpm. Various other speeds are contemplated wherein the gearing ratio is between about 10:1 to about 1:10. For example the gearing ratio (e.g., the ratio of the sun gear to the rotary driver (ring gear) can be about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10.

As best shown in FIGS. 2A and 2B, the planetary gear assembly 205 is downstream from the helical member 150 relative to the rotary driver 25. As such, the rotary driver 25 is able to rotate the helical member 150 at a first rotational speed and the planetary gear assembly 205 is able to gear-up or gear-down the first rotational speed to a third rotational speed of the elongated inner member 320 that is faster or slower than the first rotational speed (e.g., four times faster, six times faster, ten times faster, etc.). Further, because the helical member 150 is upstream from the planetary gear assembly 205, the velocity and/or acceleration of the linear movement of the helical member 150 and of the elongated inner member 320 is not impacted by the planetary gear assembly 205. That is, the linear velocity and linear acceleration of the helical member 150 is the same as the linear velocity and linear acceleration of the elongated inner member 320.

Figure 10C:
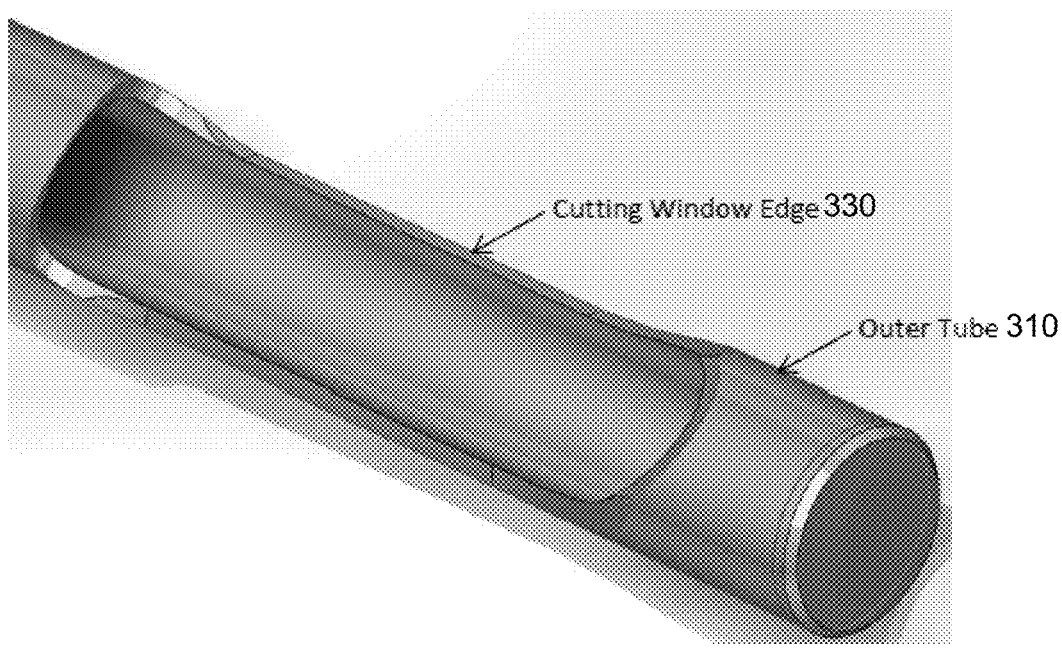
FIG. 10C is a perspective view of the elongated outer member of FIG. 10A.

As shown in FIGS. 10A-10C, the cutting window 330 has a generally oblong shape. The proximal end 331 of the cutting window 330 is saddle shaped that can form a hook 335 and the distal end 332 of the cutting window 330 is U-shaped that can form a hook. The distal end 332 is chamfered to provide a sharp edge. In some implementations, the hook 335 of cutting window 330 can have a sharpened edge to be used to pierce targeted tissue and hold the tissue as the elongated inner member 320 cuts the tissue The cutting window 330 has a length, L, over which the inner member 320 can be exposed. In other implementations, the entire cutting window 330 can have a sharped edge to aid in the piercing of targeted tissue.

Figure 11A:
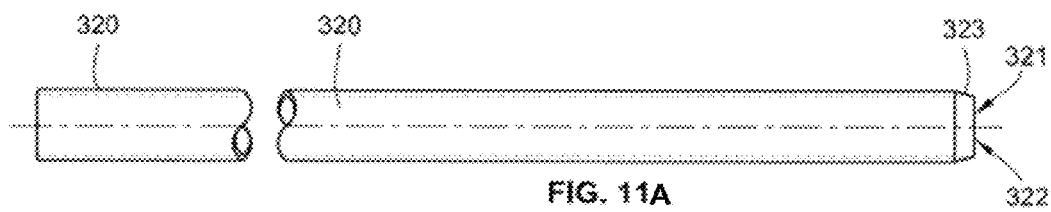
FIG. 11A is a partial top plan view of an elongated inner member of the cutting device of the cutting device of FIGS. 2A and 2B.

FIG. 11A shows that the elongated inner member 320 is generally tubular with the hollow interior or lumen 321. Aspiration of debris (e.g., cut and detached tissue and/or fluid) occurs through the hollow interior or lumen 321 of the elongated inner member 320, through the lumen 223 of the sun gear 220, and through the lumen 159 of the helical member 150 to the aspiration opening 132 of the inner hub 130. The distal end 322 of the elongated inner member 320 is chamfered to a sharp cutting edge 323 for cutting tissue. The cutting surface of the distal end 322 of the elongated inner member 320 shears tissue as the elongated inner member 320 rotates and moves linearly across the length, L, of the cutting window 330 of the elongated outer member 310. The distal end 322 or tip of the elongated inner member 320 is substantially flat.

Figures 11B, 11C:
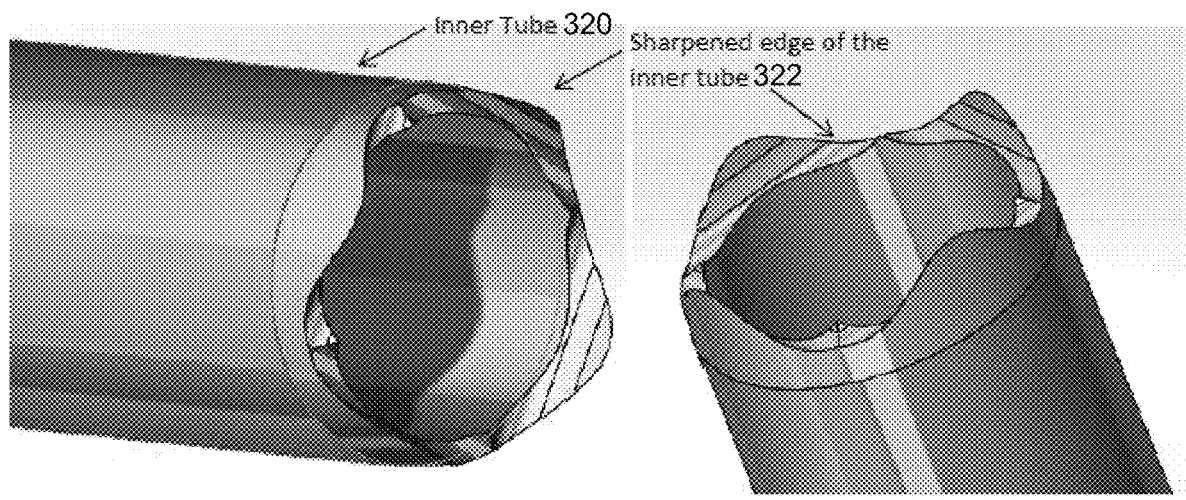
FIG. 11B is a perspective view of an elongated inner member in accordance with an another embodiment of the cutting device.
FIG. 11C is another perspective view of the elongated inner member of FIG. 11B.

Referring to FIGS. 11B and 11C, the distal end 322 of the elongated inner member 320 has a wave form tip. The wave form tip 322 has a sharpened edge that allows the elongated inner member 320 to hold onto target tissue while the cutting surface holds and slices through the tissue. Some embodiments have a single bevel edge. It is challenging to machine an inner bevel with a hard material such as 440C SS. This geometry can be created using wire-EDM and allow the device to have a double bevel edge.

Figure 12:
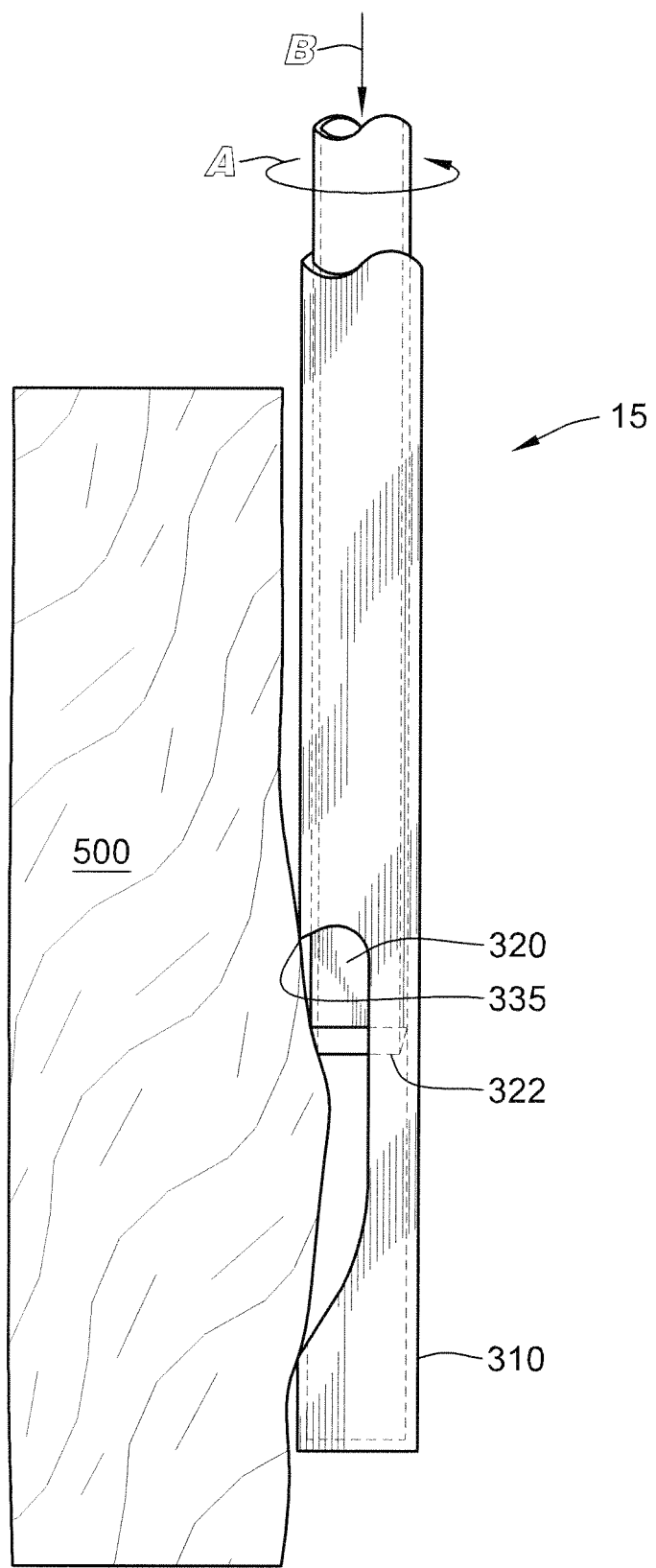
FIG. 12 is a partial side view illustrating the elongated inner member of FIG. 11 moving relative to the elongated outer member of FIGS. 10A and 10B to cut and detach tissue.

For example, referring to FIG. 12, the cutting device 15 is placed tangentially against targeted tissue 500 such that the cutting window 330 exposes the elongated inner member 320 to the tissue 500. As the elongated inner member 320 rotates and moves linearly, as shown by arrows A and B, respectively, the tissue 500 within the cutting window 330 catches on the hook 335 and then the sharp cutting edge 323 of the elongated inner member 320 shears the tissue 500 as the elongated inner member 320 advances linearly in the direction of Arrow A. The cut is completed as the cutting sharp edge 323 of the elongated inner member 320 advances beyond the distal end 332 of the cutting window 330 within the elongated outer member 310.

A number of implementations have been described. Nevertheless, it will be understood that various modifications may be made. For example, instead of a double helical channel, the helical member 150 may include a single helical channel with a retractable follower and spring, or possibly, attraction and repelling forces of magnets or a solenoid could enable the rotating and linear movements. Also, alternatively, the elongated inner and outer members 320, 310 may have a cross-sectional shape other than circular. Additionally, the shape of the hook 335 of the elongated outer member 310 may be modified in order to improve grasping of the tissue 500 or grasping a larger volume of tissue 500. Accordingly, other implementations are within the spirit and scope of the present disclosure as recited in the following claims.

A number of implementations have been described. Nevertheless, it will be understood that various modifications may be made. For example, instead of a double helical channel, the helical member may include a single helical channel with a retractable follower and spring, or possibly, attraction and repelling forces of magnets or a solenoid could enable the rotating and reciprocating movements. Also, alternatively, the inner and outer members may have a cross-sectional shape other than circular. Additionally, the shape of the hook of the outer member may be modified in order to improve grasping of the tissue or grasping a larger volume of tissue. Accordingly, other implementations are within the scope of the following claims.

What is claimed is:

1. A system for removing tissue, comprising:
    a drive coupler configured to connect to a rotary driver such that a rotational output at a first rotational speed provided by the rotary driver drives rotation of the drive coupler at the first rotational speed;
    an outer member;
    an inner member at least partially received within the outer member; and
    a plurality of gears defining a planetary gear arrangement operably coupled between the drive coupler and the inner member such that, in response to rotation of the drive coupler at the first rotational speed, the inner member is rotated relative to the outer member at a second rotational speed different from the first rotational speed,
    wherein the planetary gear arrangement is configured to translate relative to the drive coupler while maintaining the operable coupling of the planetary gear arrangement between the drive coupler and the inner member.

2. The system according to claim 1, wherein the drive coupler is configured to releasably operably connect to the rotary driver.

3. The system according to claim 1, wherein the rotary driver includes a motor.

4. The system according to claim 1, wherein the planetary gear arrangement includes a ring gear, a plurality of planetary gears, and a sun gear.

5. The system according to claim 1, wherein the planetary gear arrangement defines a gearing ratio of about 1:10 to about 10:1.

6. The system according to claim 1, wherein the first rotational speed is greater than the second rotational speed.

7. The system according to claim 1, wherein the first rotational speed is less than the second rotational speed.

8. A system for removing tissue, comprising:
    a drive coupler;
    a rotary driver configured to operably connect to the drive coupler to drive rotation of the drive coupler;
    an outer member;
    an inner member at least partially received within the outer member, the inner member and the drive coupler coaxially disposed about an axis;
    a plurality of gears operably coupled between the drive coupler and the inner member such that rotational driving of the drive coupler drives rotation of the inner member relative to the outer member; and
    a helical member and follower operably coupled between the drive coupler and the inner member such that rotational driving of the drive coupler drives translation of the inner member relative to the outer member independently of the rotation of the inner member relative to the outer member.

9. The system according to claim 8, wherein the plurality of gears is configured such that, in response to rotation of the drive coupler at a first rotational speed, the inner member is rotated relative to the outer member at a second rotational speed different from the first rotational speed.

10. The system according to claim 9, wherein the plurality of gears defines a gearing ratio of about 1:10 to about 10:1.

11. The system according to claim 9, wherein the first rotational speed is greater than the second rotational speed.

12. The system according to claim 9, wherein the first rotational speed is less than the second rotational speed.

13. The system according to claim 8, wherein the drive coupler is configured to releasably operably connect to the rotary driver.

14. The system according to claim 8, wherein the rotary driver includes a motor.

15. A system for removing tissue, comprising:
    a motor configured to provide a rotational output at a first rotational speed; and
    a resector configured to operably connect to the motor, the resector including:
        a drive coupler configured to receive the rotational output and, in response thereto, to rotate at the first rotational speed;
        a cutting member, the cutting member and the drive coupler coaxially disposed about an axis; and
        a plurality of gears operably coupled between the drive coupler and the cutting member such that, in response to rotation of the drive coupler about the axis at the first rotational speed, the cutting member is rotated about the axis at a second rotational speed different from the first rotational speed,
        wherein the cutting member is configured to translate relative to the drive coupler during the rotation of the cutting member at the second rotational speed.

16. The system according to claim 15, wherein the motor is disposed within a handpiece.

17. The system according to claim 15, wherein the plurality of gears defines a gearing ratio of about 1:10 to about 10:1.

18. The system according to claim 15, wherein the first rotational speed is greater than the second rotational speed.

19. The system according to claim 15, wherein the first rotational speed is less than the second rotational speed.

\* \* \* \* \*